US011572339B2

(12) United States Patent
Mondal

(10) Patent No.: US 11,572,339 B2
(45) Date of Patent: Feb. 7, 2023

(54) AMPHETAMINE CARBAMATE COMPOUNDS AND METHODS

(71) Applicant: NOVEN PHARMACEUTICALS, INC., Miami, FL (US)

(72) Inventor: Deboprosad Mondal, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

(21) Appl. No.: 17/569,872

(22) Filed: Jan. 6, 2022

(65) Prior Publication Data

US 2022/0213029 A1 Jul. 7, 2022

Related U.S. Application Data

(60) Provisional application No. 63/134,852, filed on Jan. 7, 2021.

(51) Int. Cl.
*C07C 269/08* (2006.01)
*G01N 30/06* (2006.01)
*G01N 30/64* (2006.01)
*G01N 30/02* (2006.01)

(52) U.S. Cl.
CPC ........... *C07C 269/08* (2013.01); *G01N 30/06* (2013.01); *G01N 30/64* (2013.01); *G01N 2030/027* (2013.01); *G01N 2030/067* (2013.01); *G01N 2030/645* (2013.01)

(58) Field of Classification Search
None
See application file for complete search history.

(56) References Cited

U.S. PATENT DOCUMENTS

| 3,742,022 A | 6/1973 | Verbiscar |
| 7,993,671 B2 | 8/2011 | Mantelle et al. |
| 8,187,628 B2 | 5/2012 | Houze et al. |
| 8,343,538 B2 | 1/2013 | Kanios et al. |
| 8,591,941 B2 | 11/2013 | Kanios et al. |
| 8,703,175 B2 | 4/2014 | Kanios et al. |
| 8,815,281 B2 | 8/2014 | Kanios et al. |
| 9,155,712 B2 | 10/2015 | Kanios et al. |
| 9,333,263 B2 | 5/2016 | Kanios |
| 9,456,993 B2 | 10/2016 | Lambert |
| 9,474,722 B2 | 10/2016 | Lambert |
| 9,901,552 B2 | 2/2018 | Lambert |
| 10,004,696 B2 | 6/2018 | Lambert |
| 10,231,938 B2 | 3/2019 | Kanios et al. |

(Continued)

FOREIGN PATENT DOCUMENTS

| WO | WO-2005/042055 A2 | 5/2005 |
| WO | WO-2014/066585 A1 | 5/2014 |
| WO | WO-2014/105783 A1 | 7/2014 |

OTHER PUBLICATIONS

International Search Report and Written Opinion in PCT Appl. No. PCT/US2022/011377 dated May 13, 2022 (14 pages).

(Continued)

*Primary Examiner* — Daniel S Larkin
(74) *Attorney, Agent, or Firm* — Foley & Lardner LLP

(57) ABSTRACT

Described herein are the amphetamine-related compounds amphetamine carbamate (amphetammonium-amphetacarbamate) and amphetacarbamate, methods of making them, methods for detecting or quantitatively determining the amount of amphetacarbamate or amphetamine carbamate in a compositions, and ion chromatography columns useful in such methods.

23 Claims, 11 Drawing Sheets

(56) References Cited

U.S. PATENT DOCUMENTS

| | | |
|---|---|---|
| 10,406,115 B2 | 9/2019 | Zhang et al. |
| 10,406,116 B2 | 9/2019 | Zhang et al. |
| 2005/0019385 A1 | 1/2005 | Houze |
| 2005/0169977 A1 | 8/2005 | Kanios et al. |
| 2014/0271865 A1 | 9/2014 | Lambert et al. |
| 2014/0288038 A1 | 9/2014 | Kanios |
| 2014/0322298 A1 | 10/2014 | Nguyen et al. |
| 2015/0104495 A1 | 4/2015 | Nguyen et al. |
| 2015/0342899 A1 | 12/2015 | Kulakofsky et al. |
| 2016/0030362 A1 | 2/2016 | Liao et al. |
| 2016/0256406 A1 | 9/2016 | Liu et al. |
| 2017/0065535 A1 | 3/2017 | Kanios |
| 2018/0207280 A1 | 7/2018 | Nguyen et al. |
| 2018/0243242 A1 | 8/2018 | Lambert |
| 2020/0277424 A1 | 9/2020 | Liao et al. |

OTHER PUBLICATIONS

International Search Report and Written Opinion in PCT Appl. No. PCT/US2022/011378 dated Jul. 4, 2022 (20 pages).

Neish; "Substituted ammonium carbamates from alpha,beta-diarylethylamines", Recueil Des Travaux Chimiques Des Pays-Bas, vol. 68, No. 5, 1949, pp. 491-494, XP055931889.

Shriner, et al; "The synthesis of N-substituted carbamates", Journal of the Amercian Chemical Society, 74(2):549-550 (Jan. 20, 1952).

Wright, et al.; "Reactions of aralkyl amines with carbon dioxide", Journal of the American Chemical Society, Nov. 1, 1948 (Nov. 1, 1948), pp. 3865-3866, XP055931915.

U.S. Appl. No. 17/569,862, filed Jan. 6, 2022, Noven Pharmaceuticals, Inc.

Buckley et al., "α-Amino Acids as Chiral Educts for Asymmetric Products. Amino Acylation with N-Acylamino Acids," Journal of the American Chemical Society, vol. 103, No. 20, pp. 6157-6163 (1981) XP055906492,Retrieved from the Internet: URL: https://pubs.acs.org/doi/pdf/10.1021/ja00410a030 [retrieved on Mar. 29, 2022].

Jonsson et al., "A Convenient Derivatization Method for the Determination of Amphetamine and Related Drugs in Urine", Journal of Forensic Science, vol. 41, No. 1, pp. 148-151, (Jan. 1996) XP008091783.

Partial International Search Report in Application No. PCT/US2022/011378 dated Apr. 11, 2022.

Thurbide et al., "Discrimination of structural isomers of amphetamine using carbon dioxide negative-ion chemical ionization mass spectrometry", Spectroscopy, vol. 13, No. 2, pp. 151-161, (1996/1997) XP055206739.

477370, AMPHETAMINE CARBAMATE, LOT RN178-1, IN DMSO-D6 W/ TMS, 1H NMR, REFERENCED TO TMS AT 0PPM 25C

FILE: 881285

VNMRJ VERSION 3.2 REVISION A
    REV. DATE: 2012-11-09
    PATCH PSG103
OS: LINUX 6.1

DATA COLLECTION:
    SYSTEM NAME: NMR400
    CONSOLE TYPE: VNMRS-DD2-400
DATA PROCESSING:
    SYSTEM NAME: NMR400
PROCESSED BY: PATRICK WHEELER

ACQ. DATE: FEB 27 2018
    PROBE: 5MM_AONP-1
    SOLVENT: DMSO
    TEMP. : 25.0 C / 298.1 K
    SPIN RATE: 0 HZ
PULSE SEQUENCE: S2PUL
    RELAX. DELAY: 15.000 SEC
    PULSE WIDTH: 6.6 USEC (90.0 DEG.)
    ACQ. TIME: 5.000 SEC
    SPECTRAL WIDTH: 4006.4 HZ (10.021 PPM)
    100 SCANS
    ACQUIRED POINTS: 40064
OBSERVE NUCLEUS: H1 (399.8212218 MHZ)
DATA PROCESSING
    LINE BROADENING: 0.2 HZ
    FT SIZE: 262144

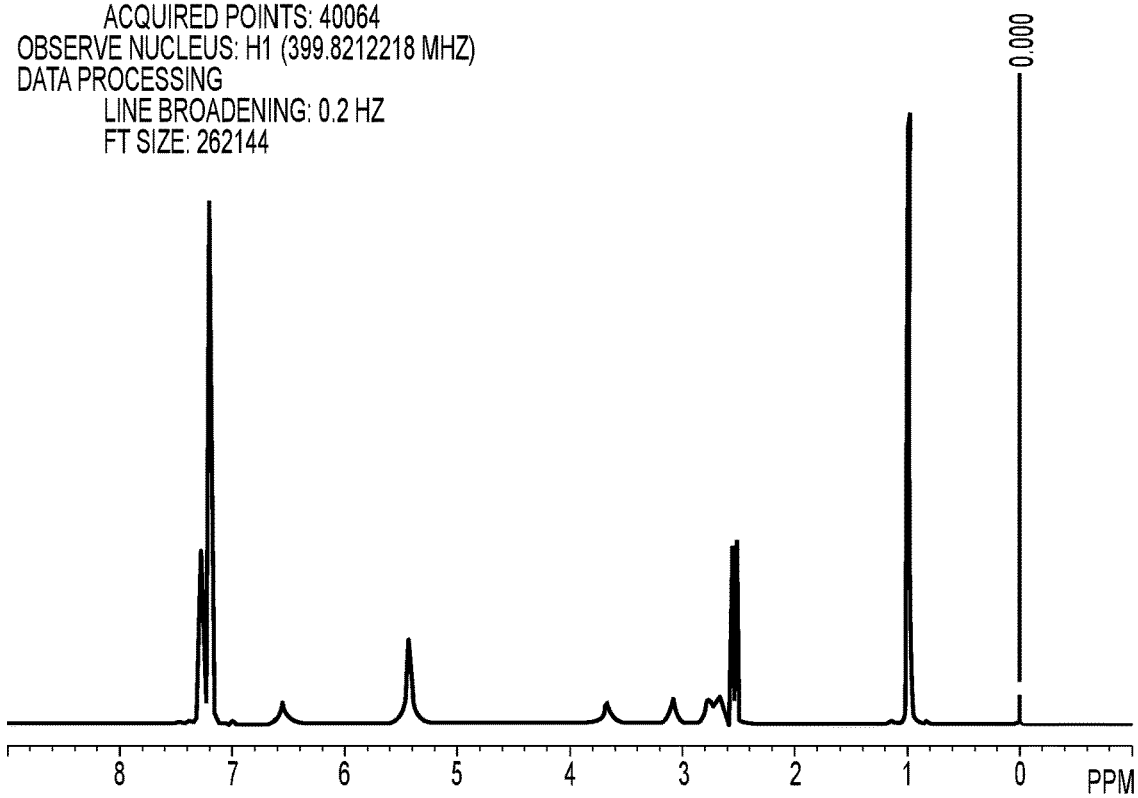

FIG. 4

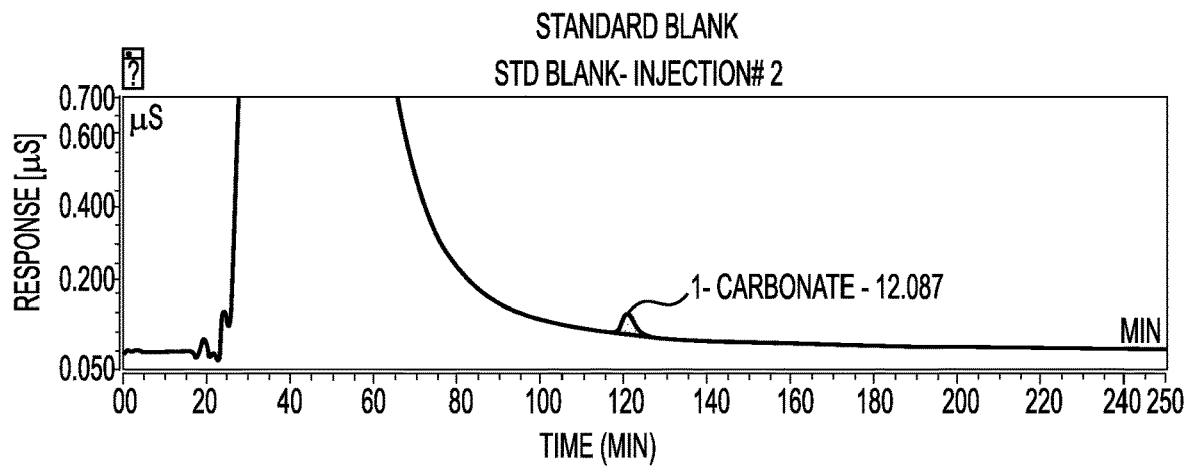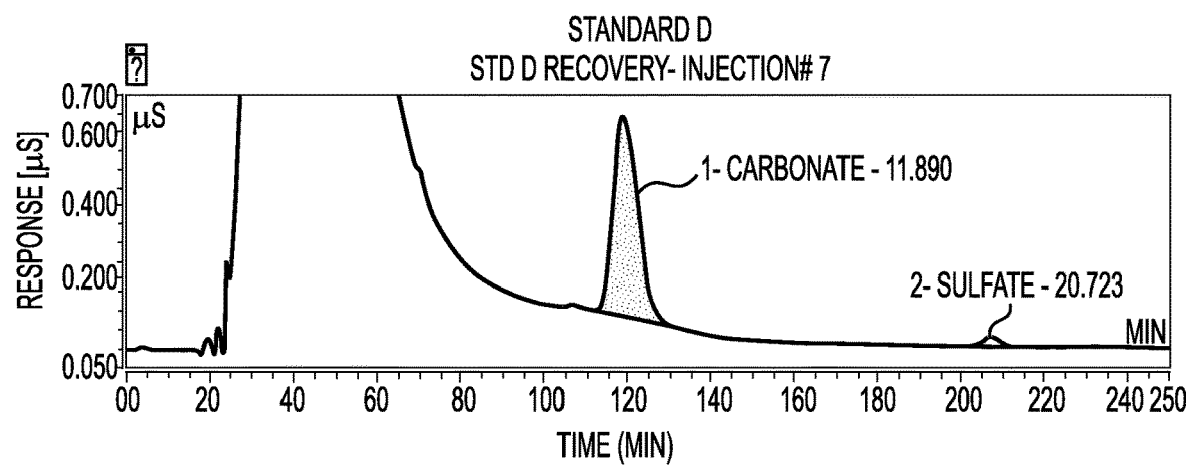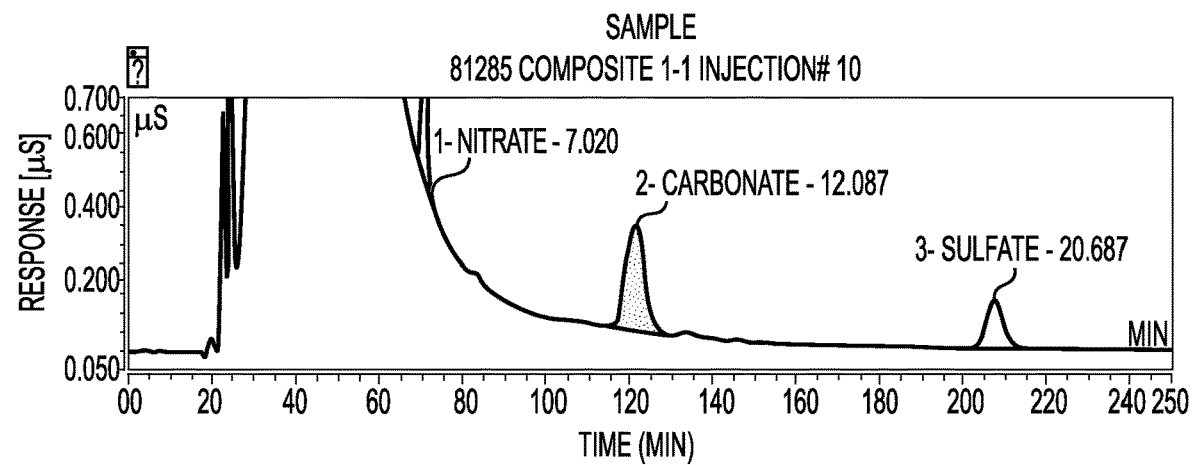
*FIG. 11*

AMPHETAMINE CARBAMATE COMPOUNDS AND METHODS

CROSS-REFERENCE TO RELATED APPLICATIONS

The present application claims priority to U.S. provisional application 63/134,852, filed Jan. 7, 2021, the entire contents of which are incorporated herein by reference.

FIELD

The present disclosure relates generally to newly discovered amphetamine-related compounds, amphetamine carbamate (amphetammonium-amphetacarbamate) and amphetacarbamate, and methods of detecting and quantitating the presence of the same in compositions, including amphetamine-containing compositions, including transdermal amphetamine compositions and amphetamine transdermal delivery systems. The methods use ion chromatography to detect and quantitate carbonate ion formed by an in situ reaction of amphetacarbamate. Ion chromatography columns useful in such methods also are described herein.

BACKGROUND

Attention-deficit/hyperactivity disorder (ADHD) is a neurobehavioral disorder that typically begins in childhood and often persists into adulthood. ADHD is characterized by developmentally inappropriate levels of inattention, impulsivity, and hyperactivity. Although individuals with this disorder can be very successful in life, without identification and proper treatment, ADHD may have serious consequences, including school failure, family stress and disruption, depression, problems with relationships, substance abuse, delinquency, risk for accidental injuries and job failure. Thus, early identification and treatment can be extremely important to a subject's quality of life.

ADHD is the most common developmental disorder of childhood, affecting about 3 to 5% of children globally and diagnosed in about 2 to 16% of school aged children. In addition, it is estimated that 4.7% of American adults live with ADHD. Amphetamine products currently approved for use in the U.S. for the treatment of ADHD are oral dosage forms, including ADDERALL XR® (amphetamine, d-amphetamine mixed salts) and VYVANSE® (lisdexamfetamine) (a prodrug of amphetamine).

Transdermal amphetamine compositions and amphetamine transdermal delivery systems have been described in previous patents and patent applications, for example, in U.S. Pat. Nos. 7,993,671; 8,632,02; 8,216,606; 9,034,370; 8,337,884; 8,187,628; 8,916,191; 8,591,941; 8,815,281; 9,155,712; 10,231,938; 9,333,263; 9,456,993; 9,474,722; 9,901,552; 10,004,696, U.S. Patent Application Publication 2015/0104495; U.S. Pat. Nos. 8,703,175; 9,295,726; U.S. Patent Application Publication 2015/0342899. However, there is no approved transdermal amphetamine product. Thus, there remains a need for transdermal amphetamine compositions and amphetamine transdermal delivery systems. For potency and safety reasons, there is a particular need for transdermal amphetamine compositions and amphetamine transdermal delivery systems that have at most low levels of amphetamine-related compounds, including the newly discovered amphetamine-related compounds, amphetamine carbamate and amphetacarbamate.

In view of these needs, there is a need for methods for detecting and quantitating amphetamine carbamate and amphetacarbamate that may be present in amphetamine-containing compositions, including transdermal amphetamine compositions and amphetamine transdermal delivery systems.

SUMMARY OF THE INVENTION

Provided herein are methods of quantitatively determining the amount of amphetacarbamate in a composition, comprising (a) subjecting a composition comprising amphetacarbamate to reaction conditions that convert the amphetacarbamate in the composition into reaction products comprising carbonate; (b) quantifying the amount of carbonate in the reaction products; and (c) quantifying the amphetacarbamate originally present in the composition from the quantified amount of carbonate in the reaction products and the stoichiometric relationship between amphetacarbamate and carbonate in the reaction of step (a). The composition at step (a) may comprise amphetamine and amphetacarbamate. The reaction conditions may comprise contacting the composition comprising amphetacarbamate with a base under an inert atmosphere. The base may be an aqueous alkali or earth alkali hydroxide salt, such potassium hydroxide (KOH), sodium hydroxide (NaOH), or lithium hydroxide (LiOH).

Also provided herein are methods of quantitatively determining the amount of amphetacarbamate in a composition by ion chromatography, comprising (a) subjecting a composition comprising amphetacarbamate to ion chromatography under an inert atmosphere with an eluent comprising a basic hydroxide ion under conditions that permit in situ reaction of the amphetacarbamate with the hydroxide ion to produce carbonate ion; (b) separating the carbonate ion via a column packed with a composition comprising alkanol quaternary ammonium cation; (c) detecting and quantifying the carbonate ion with a conductivity detector; and (d) quantifying the amphetacarbamate originally present in the composition from the quantified amount of carbonate ion based a 1:1 stoichiometric relationship between amphetacarbamate and carbonate. The composition at step (a) may comprise amphetamine and amphetacarbamate.

Also provided herein are methods of detecting the presence of amphetacarbamate in a composition comprising amphetamine by ion chromatography, comprising (a) subjecting a composition comprising amphetamine to ion chromatography under an inert atmosphere with an eluent comprising basic hydroxide ion under conditions that permit in situ reaction of any amphetacarbamate present in the composition with the hydroxide ion to obtain carbonate ion; (b) separating any carbonate ion via a column packed with a composition comprising alkanol quaternary ammonium cation; and (c) detecting any carbonate ion with a conductivity detector; wherein the detection of carbonate ion is indicative of the presence of amphetacarbamate in the composition.

In any methods described herein, the composition at step (a) may be a solution prepared from an amphetamine active pharmaceutical ingredient composition (API).

In any methods described herein, the composition at step (a) may be a solution prepared from an amphetamine-containing polymer matrix by a process comprising (i) immersing the drug-containing polymer matrix comprising amphetamine, amphetacarbamate, and polymer components in an organic solvent, to obtain an extraction mixture; (ii) subjecting the extraction mixture to sonication; (iii) adding a sample diluent to the extraction mixture to induce precipitation of the polymer components while maintaining the amphetamine and amphetacarbamate in solution, to obtain a composition comprising a precipitate; (iv) filtering the composition comprising a precipitate to remove the precipitate, thereby obtaining a composition comprising amphetamine and amphetacarbamate in solution. One or more of steps (i)-(iv) may be conducted under an inert atmosphere. The organic solvent may be inert gas-purged methanol; additionally or alternatively, the sample diluent may consist of a mixture of the organic solvent and water, that also may be gas-purged. The organic solvent may be inert gas-purged methanol and the sample diluent may consist of a mixture of inert gas-purged methanol and reagent grade water. In specific embodiments, the organic solvent is helium-purged methanol and the sample diluent consists of a mixture of helium-purged methanol and reagent grade water. The amphetamine-containing polymer matrix may be a drug-containing polymer matrix of an amphetamine transdermal delivery system.

In any embodiments of the IC methods the eluent may be inert-gas purged deionized water spiked with KOH. In specific embodiments, the eluent is helium-gas purged deionized water spiked with KOH.

In any embodiments described herein, the composition may comprise d-amphetamine, l-amphetamine, or both. In any embodiments described herein, the composition may comprise d-amphetacarbamate, l-amphetacarbamate, or both. In any embodiments described herein, the composition may comprise d-amphetammonium-d-amphetacarbamate, l-amphetammonium-l-amphetacarbamate, or both.

Also provided are ion chromatography columns comprising: a resin comprising alkanol quaternary ammonium cations; an aqueous solution comprising basic hydroxide ion; and two or more selected from amphetacarbamate, amphetamine and carbonate. The aqueous solution may comprise deionized water that has been purged with an inert gas. Each of amphetacarbamate, amphetamine, and carbonate may be present in the column.

Also provided is isolated amphetamine carbamate (amphetammonium-amphetacarbamate) having the following chemical structure:

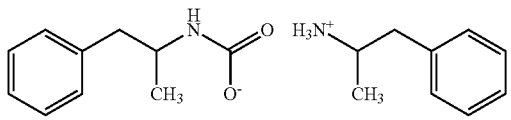

Also provided is isolated d-amphetamine carbamate (d-amphetammonium-d-amphetacarbamate) having the following chemical structure:

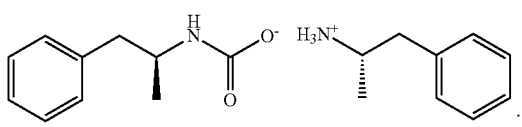

The isolated d-amphetamine carbamate may be in crystalline form and have one or more of a high resolution mass spectrum (MS) of FIG. 3, a $^1$H NMR spectrum of FIG. 4, a $^{13}$C NMR spectrum of FIG. 5, a single crystal powder x-ray diffraction having three or more major peaks that are in the pattern of FIG. 6, a packing diagram for crystalline amphetamine carbamate viewed along the crystallographic b axis of FIG. 7, and a calculated x-ray powder diffraction pattern of FIG. 8, having three or more major peaks that are identical (or within ±0.2 degrees 2Θ) as peaks in the pattern of FIG. 9, and a TG-DSC of FIG. 10.

Also provided is isolated l-amphetamine carbamate (l-amphetammonium-l-amphetacarbamate).

Also provided is isolated amphetamine carbamate obtained by a process comprising removing a crystal comprised of amphetamine carbamate from a drug-containing polymer matrix comprising amphetamine in a polymer matrix. The polymer matrix my comprise one or more acrylic pressure-sensitive adhesives. The polymer matrix may consist of the amphetamine, one or more acrylic pressure-sensitive adhesive, and amphetamine carbamate. The isolated amphetamine carbamate may be d-amphetamine carbamate, such as when the polymer matrix comprises d-amphetamine. The isolated d-amphetamine carbamate may be in crystalline form and have one or more of a high resolution mass spectrum (MS) of FIG. 3, a $^1$H NMR spectrum of FIG. 4, a $^{13}$C NMR spectrum of FIG. 5, a single crystal powder x-ray diffraction having three or more major peaks that are in the pattern of FIG. 6, a packing diagram for crystalline amphetamine carbamate viewed along the crystallographic b axis of FIG. 7, and a calculated x-ray powder diffraction pattern of FIG. 8, having three or more major peaks that are identical (or within ±0.2 degrees 2Θ) as peaks in the pattern of FIG. 9, and a TG-DSC of FIG. 10.

The isolated amphetamine carbamate may be l-amphetamine carbamate, such as when the polymer matrix comprises l-amphetamine. The isolated l-amphetamine carbamate may be in crystalline form.

Also provided is isolated amphetamine carbamate obtained by a process comprising exposing amphetamine to carbon dioxide. The isolated amphetamine carbamate may be d-amphetamine carbamate, such as when the amphetamine is d-amphetamine. The isolated d-amphetamine carbamate may be in crystalline form and have one or more of a high resolution mass spectrum (MS) of FIG. 3, a $^1$H NMR spectrum of FIG. 4, a $^{13}$C NMR spectrum of FIG. 5, a single crystal powder x-ray diffraction having three or more major peaks that are in the pattern of FIG. 6, a packing diagram for crystalline amphetamine carbamate viewed along the crystallographic b axis of FIG. 7, and a calculated x-ray powder diffraction pattern of FIG. 8, having three or more major peaks that are identical (or within ±0.2 degrees 2Θ) as peaks in the pattern of FIG. 9, and a TG-DSC of FIG. 10. The isolated amphetamine carbamate may be l-amphetamine carbamate, such as when the amphetamine is l-amphetamine. The isolated l-amphetamine carbamate may be in crystalline form.

BRIEF DESCRIPTION OF THE DRAWINGS

FIG. 2A illustrates the overall reaction scheme; FIG. 2B illustrates intermediate steps.

FIG. 4 sets forth results of a $^1$H NMR spectral analysis of d-amphetamine carbamate.

FIG. 11 sets forth a typical chromatogram for a standard diluent blank ("Standard Blank"), a carbonate working standard solution ("Standard D"), and a sample prepared from an amphetamine transdermal drug delivery system.

DETAILED DESCRIPTION

Figure 1:
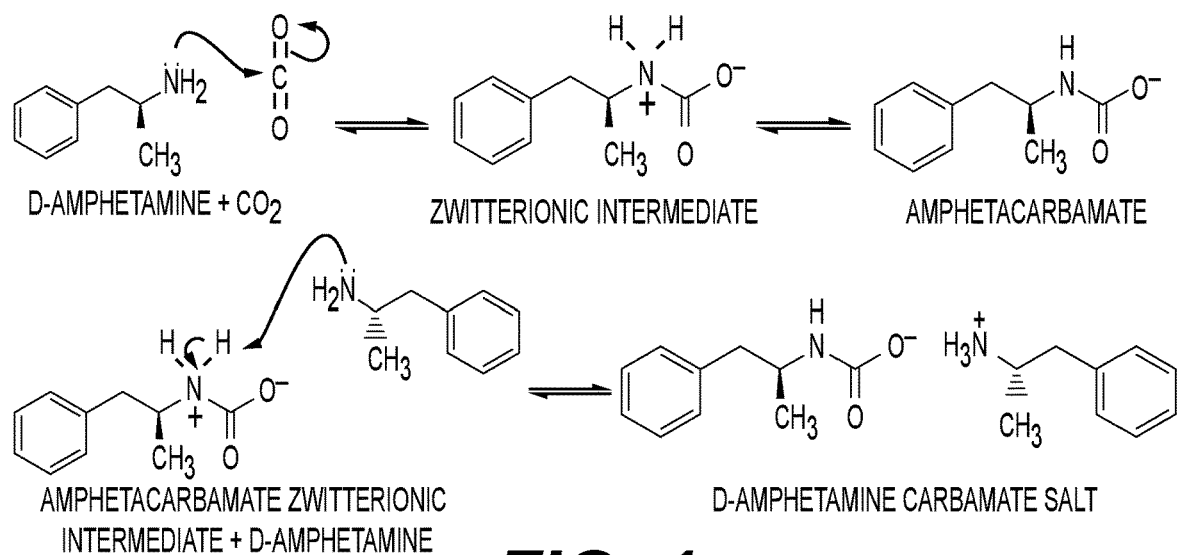
FIG. 1 illustrates a reaction scheme for the reaction of d-amphetamine with carbon dioxide to form d-amphetacarbamate which associates with ionized amphetamine (amphetammonium) to form d-amphetamine carbamate (d-amphetammonium-d-amphetacarbamate).

Described herein are two newly discovered amphetamine-related compounds (which exist in optical isomer forms), amphetamine carbamate (amphetammonium-amphetacarbamate) and amphetacarbamate, and methods of detecting and quantitating the presence of the same in compositions, including amphetamine-containing compositions, including transdermal amphetamine compositions and amphetamine transdermal delivery systems. In specific embodiments, the methods use ion chromatography to detect and quantitate carbonate ion formed by an in situ reaction of amphetacarbamate. Ion chromatography columns useful in such methods also are described herein.

Definitions

Technical and scientific terms used herein have the meanings commonly understood by one of ordinary skill in the art to which the present invention pertains, unless otherwise defined. Reference is made herein to various methodologies known to those of ordinary skill in the art. Except where otherwise noted or described as part of the present disclosure, any suitable materials and/or methods known to those of ordinary skill in the art can be utilized in carrying out the present invention. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein means that the described composition (e.g., polymer matrix, etc.) comprises less than 1% by weight, based on the total weight of the composition at issue, of the excluded component(s). In some embodiments, a composition "substantially free of" excluded component(s) may be prepared without the excluded component(s), but a small amount of excluded component(s) may be present as contaminant(s), by-product(s), degradation product(s), etc.

The transdermal amphetamine compositions described herein are in a "flexible, finite form." As used herein, the phrase "flexible, finite form" means a substantially solid form capable of conforming to a surface with which it comes into contact, and capable of maintaining contact so as to facilitate topical application, such as a film or patch. The transdermal amphetamine compositions described herein comprise a drug-containing polymer matrix that releases amphetamine upon application to the skin.

As used herein, the term "transdermal delivery system" refers to transdermal amphetamine compositions described herein that include a backing layer in addition to the drug-containing polymer matrix layer. Transdermal delivery systems per se are known in the art and commercially available, and often referred to as transdermal "patches."

As used herein, "active surface area" means the surface area of the drug-containing polymer matrix of the transdermal composition or transdermal delivery system.

In some embodiments, the transdermal delivery systems may include a release liner in addition to a drug-containing polymer matrix layer and backing layer. When present, a release liner is removed prior to use, i.e., prior to application to a skin surface of a subject.

As used herein, "drug-containing polymer matrix" refers to a polymer composition which contains one or more drugs, such as amphetamine, and a polymer, such as a pressure-sensitive adhesive polymer. As used herein, the term "pressure-sensitive adhesive" refers to a viscoelastic material which adheres instantaneously to most substrates with the application of very slight pressure and remains tacky. A polymer is a pressure-sensitive adhesive polymer if it has the properties of a pressure-sensitive adhesive per se. Other polymers may function as a pressure-sensitive adhesive by admixture with one or more tackifiers, plasticizers, cross-linking agents, and/or other excipients. Thus, in some embodiments, the polymer matrix comprises a pressure-sensitive adhesive polymer and, optionally, one or more tackifiers, plasticizers, cross-linking agents, and/or other excipients. Additionally or alternatively, in some embodiments the polymer matrix comprises a polymer that functions as a pressure-sensitive adhesive by admixture with one or more tackifiers, plasticizers, cross-linking agents, and/or other excipients. In any embodiments, the polymer matrix may include one polymer or a mixture of different polymers.

In some embodiments, the polymer matrix is a pressure-sensitive adhesive at room temperature and exhibits desirable physical properties, such as good adherence to skin, ability to be peeled or otherwise removed without substantial trauma to the skin, retention of tack with aging, etc. In some embodiments, the polymer matrix has a glass transition temperature ($T_g$), measured using a differential scanning calorimeter, of between about −70° C. and about 0° C.

In some embodiments, the transdermal compositions in flexible, finite form or transdermal delivery systems are "monolithic" or "monolayer" systems, such that the drug-containing polymer matrix layer is the only polymeric layer present other than the backing layer and the release liner, if present. In such embodiments, the polymer matrix functions as both the drug carrier and the means of affixing the system to the skin.

Amphetamine, Amphetamine Carbamate and Amphetacarbamate

Amphetamine (alpha-methylphenethylamine) is a chiral drug. The solid oral dosage form ADDERALL® XR includes several different amphetamine salts, including amphetamine sulfate, amphetamine saccharate, and amphetamine aspartate monohydrate, in an overall ratio of d-amphetamine to l-amphetamine of 3:1. The solid oral dosage form VYVANSE® includes lisdexamfetamine, which is a prodrug of amphetamine. Transdermal amphetamine compositions and amphetamine transdermal delivery systems under development may be formulated with amphetamine free base (d-amphetamine, l-amphetamine, or a mixture thereof in any relative amounts), or any pharmaceutically acceptable salt of amphetamine, or any prodrug thereof, or any combinations thereof, and with any isomeric content, and any combinations thereof.

The subject matter of the present disclosure stems from the surprising and unexpected determination that transdermal amphetamine compositions are susceptible to the formation of crystals of amphetamine carbamate in the drug-containing polymer matrix. Neither this problem, nor the existence or identity of amphetamine carbamate per se were known. Rather, amphetamine carbamate was identified and characterized by analyzing crystals isolated from drug-containing polymer matrices of transdermal amphetamine compositions. Additionally, neither the existence or identity of amphetacarbamate per se were known. Rather, amphetacarbamate was identified during the work done to identify and characterize amphetamine carbamate.

Amphetamine carbamate (a salt) also may be referred to as amphetammonium-amphetacarbamate, to reflect the identity of the ionic species of the salt. The IUPAC name for d-amphetamine carbamate (a salt) is (S)-1-phenylpropan-2-ammonium-(S)-(1-phenylpropan-2-yl)carbamate. The IUPAC name for l-amphetamine carbamate (a salt) is (R)-1-phenylpropan-2-ammonium-(R)-(1-phenylpropan-2-yl)carbamate. Either isomer of the salt has the chemical formula $C_{19}H_{26}N_2O_2$ with a molecular weight of 314.43 g/mol. The chemical structure is set forth in FIG. 1, which depicts d-amphetamine carbamate as an example. As illustrated in FIG. 1, while not wanting to be bound by theory, it is believed that d-amphetamine reacts with carbon dioxide (e.g., atmospheric carbon dioxide) to form d-amphetacarbamate which combines with ionized d-amphetamine (d-amphetammonium) to form the crystalline material d-amphetamine carbamate. The proposed reaction pathway is set forth in FIG. 1. A parallel reaction occurs with l-amphetamine, to form l-amphetacarbamate and l-amphetamine carbamate.

The IUPAC name for d-amphetacarbamate is (S)-(1-phenylpropan-2-yl)carbamate. The IUPAC name for l-amphetacarbamate is (R)-(1-phenylpropan-2-yl)carbamate. Either isomer has the chemical formula $C_{10}H_{12}NO_2^-$ and a molecular weight of 178.21 g/mol. The chemical structure is set forth in FIG. 1, which depicts d-amphetacarbamate.

Figure 8:
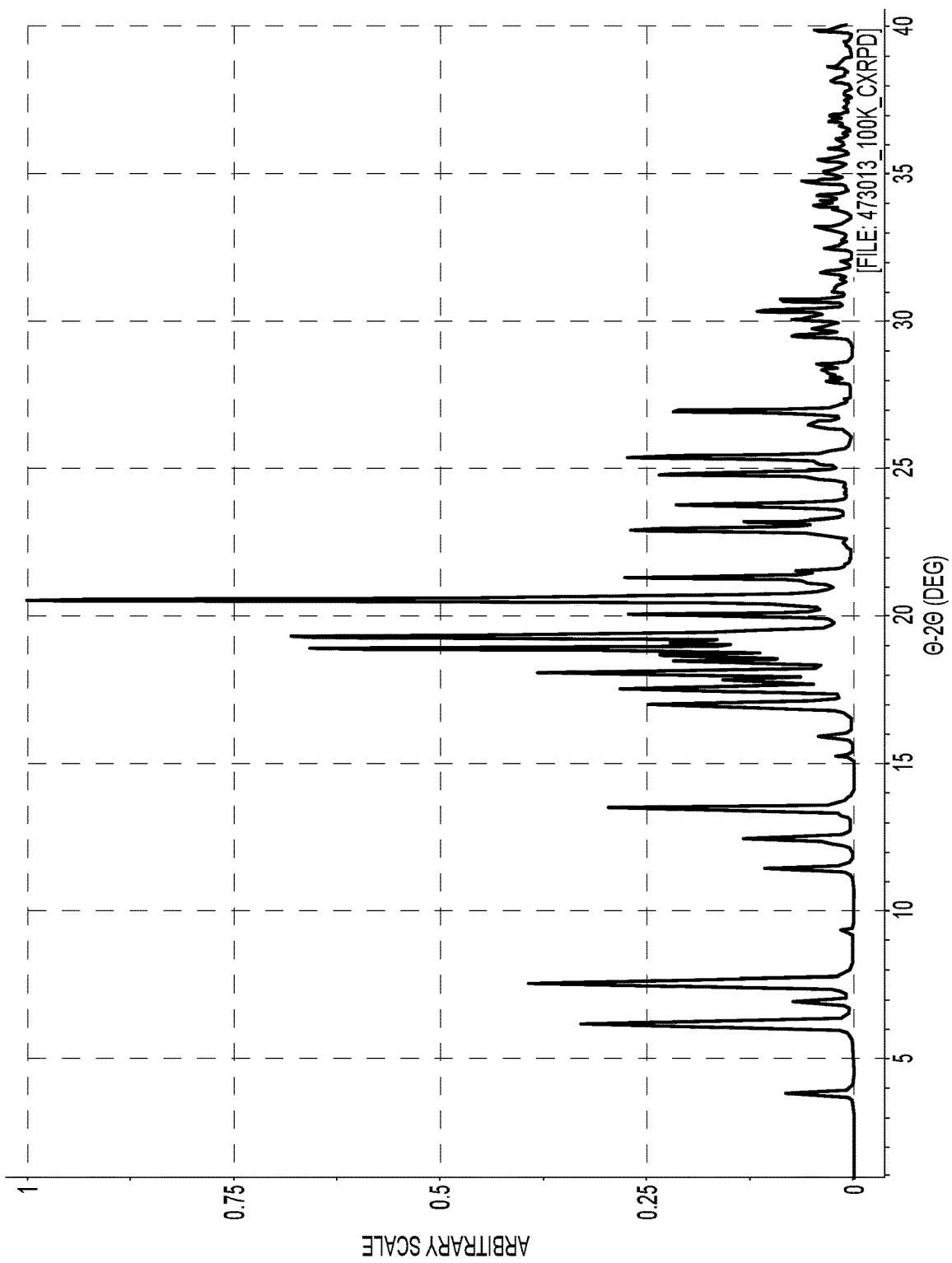
FIG. 8 sets forth a calculated x-ray powder diffraction pattern for crystalline d-amphetamine carbamate viewed along the crystallographic b axis.
Figure 9:
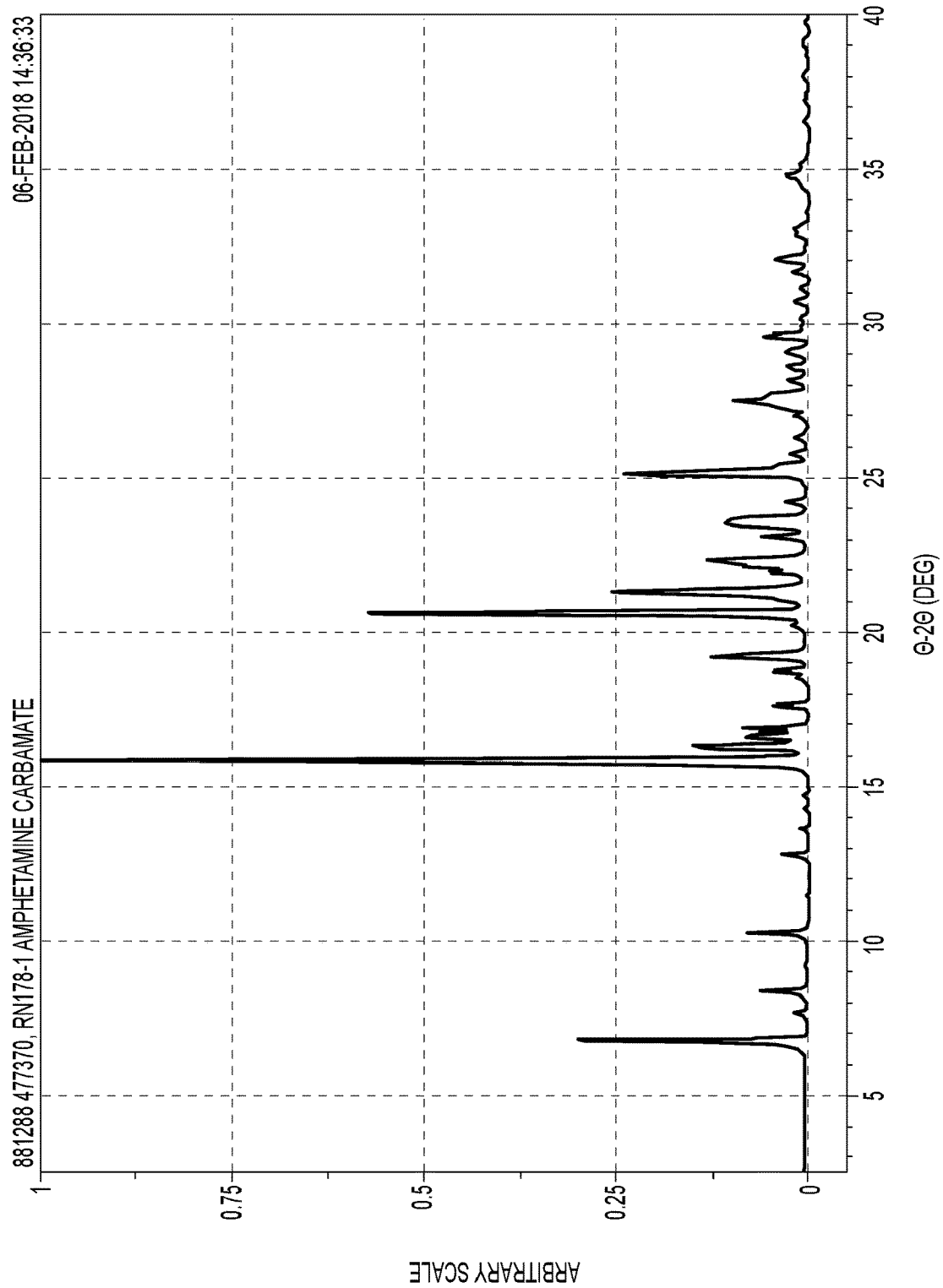
FIG. 9 sets forth a measured x-ray powder diffraction pattern for synthesized crystalline d-amphetamine carbamate.
Figure 10:
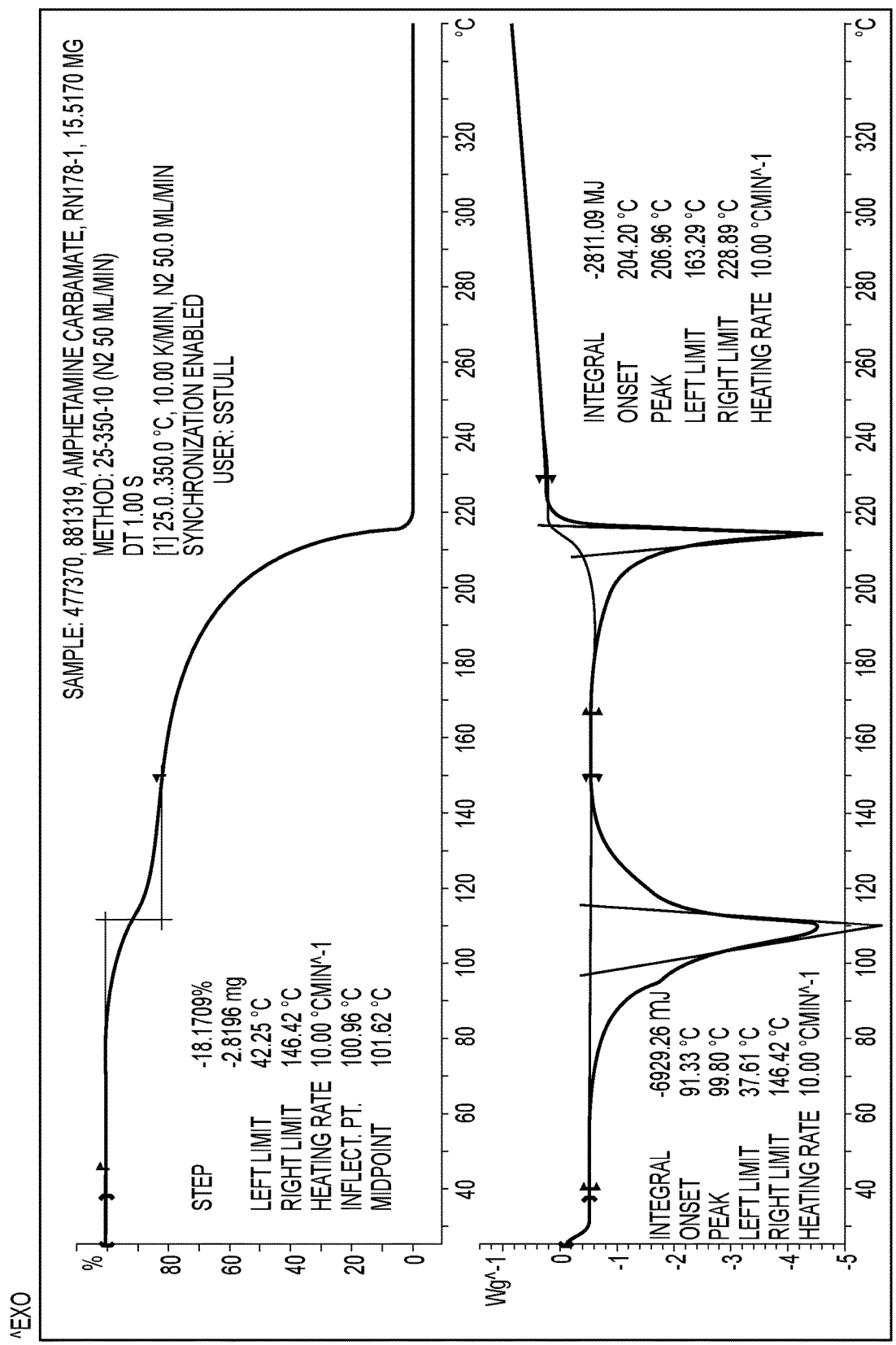
FIG. 10 sets forth a TGA/DSC thermogram of the synthesized d-amphetamine carbamate.

FIGS. 3-10 set forth characterizing data for d-amphetamine carbamate, including results of high resolution mass spectrometry (MS) analysis (FIG. 3) performed in negative ion mode (top panel) and positive ion mode (bottom panel); $^1$H NMR spectral analysis (FIG. 4), $^{13}$C NMR spectral analysis (FIG. 5), single crystal powder x-ray diffraction analysis (FIG. 6), a packing diagram for crystalline d-amphetamine carbamate viewed along the crystallographic b axis (FIG. 7), a calculated x-ray powder diffraction pattern (FIG. 8), a measured x-ray powder diffraction pattern for synthesized crystalline d-amphetamine carbamate (FIG. 9), and a TGA/DSC thermogram of the synthesized d-amphetamine carbamate (FIG. 10). Elemental analysis also was performed and consistent with the chemical structure set forth in FIG. 1.

Without wanting to be bound by theory, it is believed that any amphetacarbamate present in a drug-containing polymer matrix will be associated with ionized amphetamine (amphetammonium) present in the polymer matrix, such that the species present is amphetamine carbamate (amphetammonium-amphetacarbamate). Nevertheless, we have chosen to define amphetamine carbamate content with reference to amphetacarbamate content. This also is convenient because the stoichiometric ratio between amphetamine and amphetacarbamate in the reactions at issue (as presently understood and illustrated in FIG. 1) is 1:1. Thus, in the discussion that follows, amphetacarbamate content is discussed and quantitated, even though the species present in a dry drug-containing polymer matrix (e.g., as made, stored, sold, offered for sale or used) may be more accurately described as amphetamine carbamate (amphetammonium-amphetacarbamate). As illustrated below, the amount of amphetacarbamate present in a composition can be used to quantify the amount of amphetamine carbamate present using the molar ratio and relative molecular weights of these species.

Certain embodiments of the present disclosure include isolated amphetamine carbamate, including isolated d-amphetamine carbamate or isolated l-amphetamine carbamate or an isolated mixture of d-amphetamine carbamate and l-amphetamine carbamate. In specific embodiments, the isolated amphetamine carbamate comprises or consists of d-amphetamine carbamate having the following chemical structure:

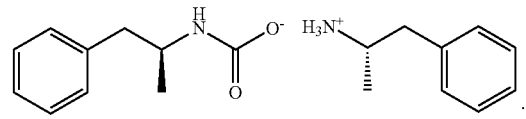

In specific embodiments, the isolated amphetamine carbamate comprises d-amphetamine carbamate substantially free of amphetamine. In specific embodiments, the isolated amphetamine carbamate comprises d-amphetamine carbamate substantially free of l-amphetamine carbamate. In specific embodiments, the isolated amphetamine carbamate comprises d-amphetamine carbamate substantially free of amphetamine and substantially free of l-amphetamine carbamate.

Figure 3:
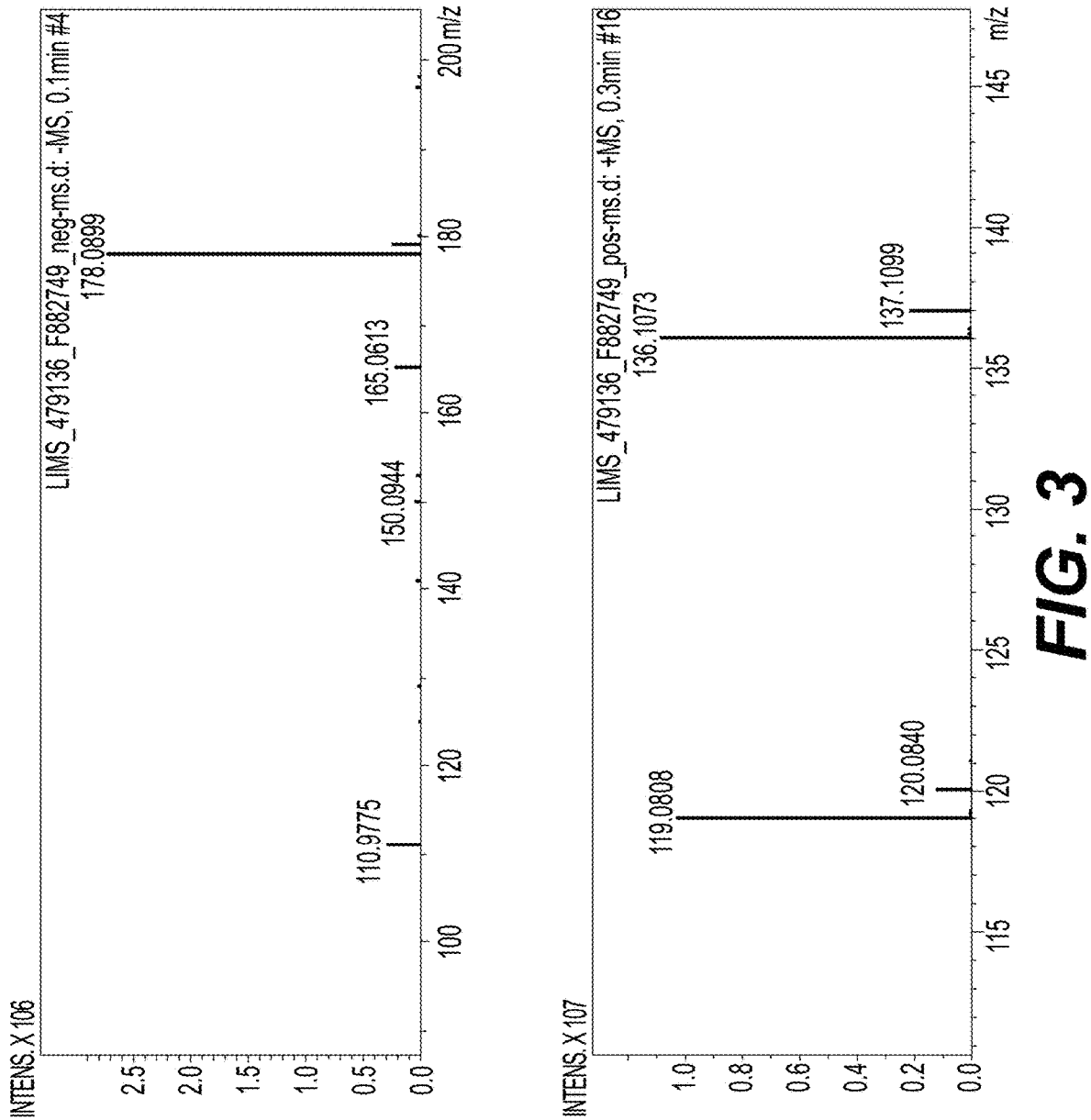
FIG. 3 sets forth results of high resolution mass spectrometry (MS) analysis of d-amphetamine carbamate performed in negative ion mode (top panel) and positive ion mode (bottom panel).
Figure 5:
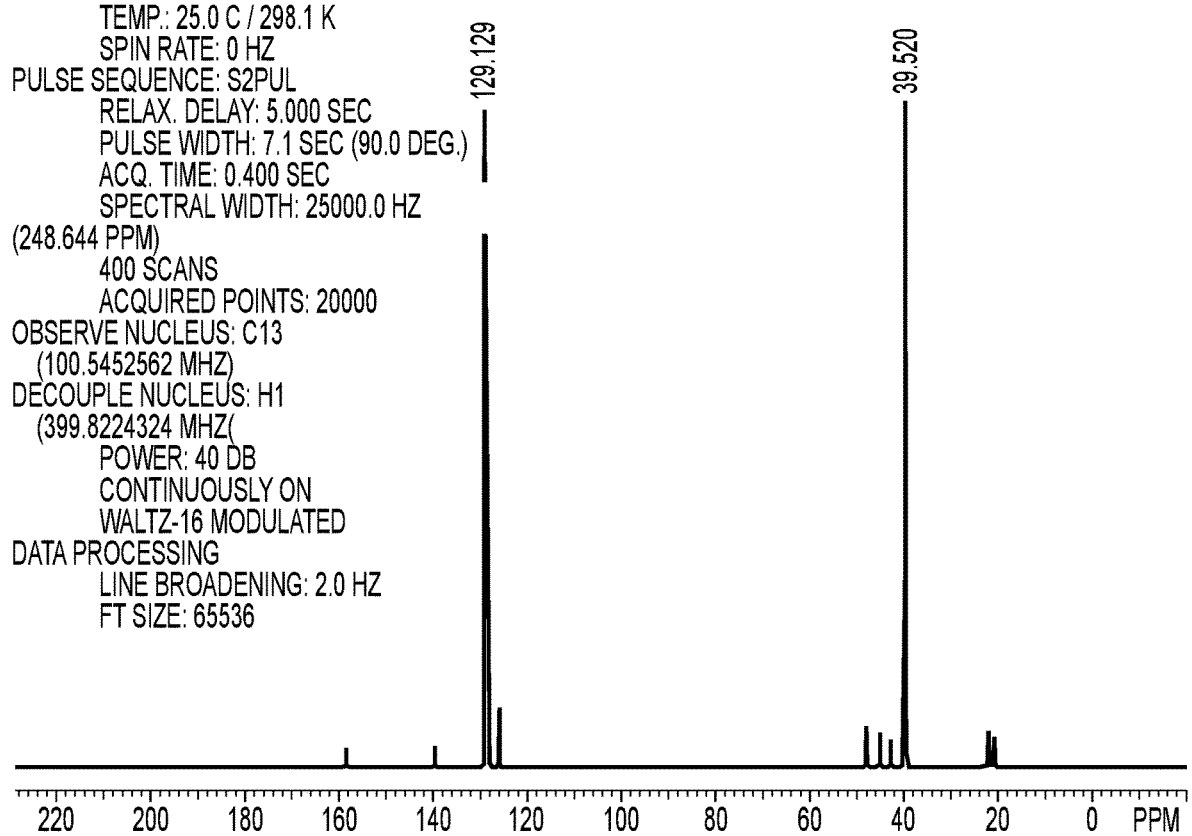
FIG. 5 sets forth results of a $^{13}$C NMR spectral analysis of d-amphetamine carbamate.
Figure 6:
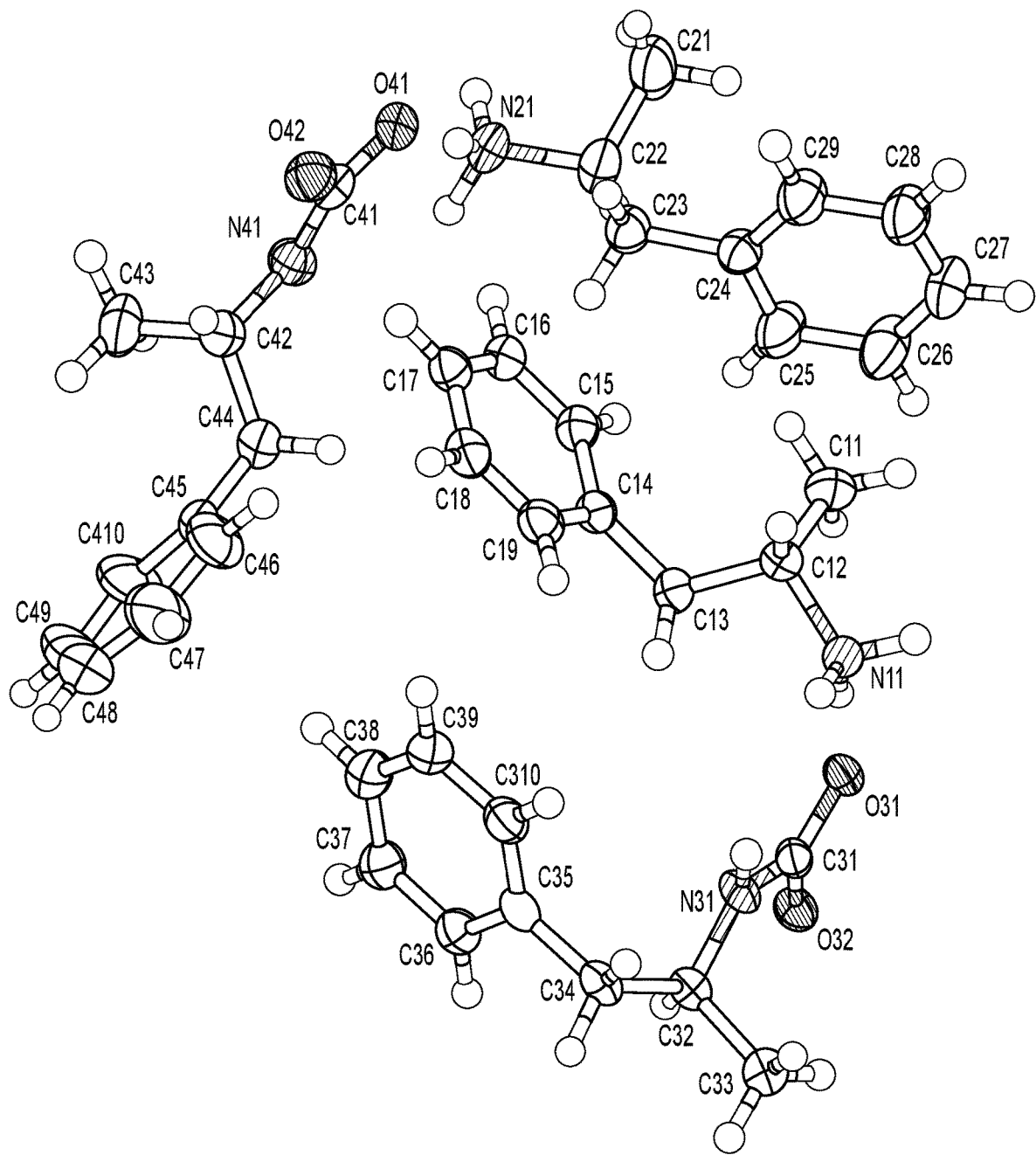
FIG. 6 illustrates the crystal structure of d-amphetamine carbamate based on single crystal powder x-ray diffraction analysis.
Figure 7:
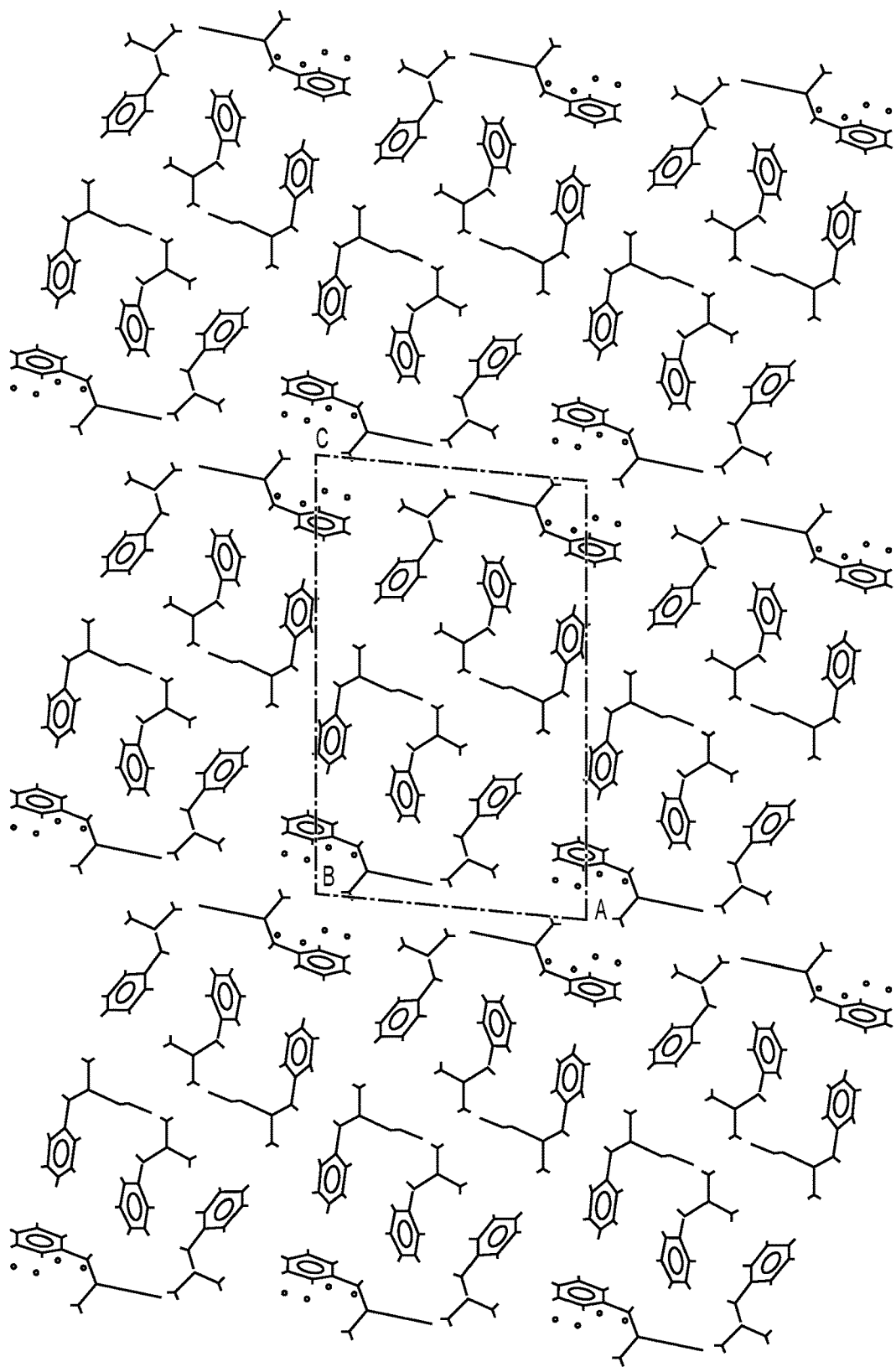
FIG. 7 provides a packing diagram for crystalline d-amphetamine carbamate viewed along the crystallographic b axis.

The isolated d-amphetamine carbamate may be in crystalline form, and have one or more of a high resolution mass spectrum (MS) as set forth in FIG. 3; a $^1$H NMR spectrum as set forth in FIG. 4; a $^{13}$C NMR spectrum as set forth in FIG. 5; a single crystal powder x-ray diffraction having three or more major peaks that are in the pattern of FIG. 6; a packing diagram for crystalline amphetamine carbamate viewed along the crystallographic b axis of FIG. 7; a calculated x-ray powder diffraction pattern as set forth in FIG. 8; a measured x-ray powder diffraction pattern having three or more major peaks that are identical to, or within ±0.2 degrees 2θ of, peaks in the x-ray powder diffraction pattern of FIG. 9, and a TG-DSC as set forth in FIG. 10. The isolated d-amphetamine carbamate in crystalline form may contain 3, 4, 5, 6, 7, 8, or 9 major peaks that are identical to, or within ±0.2 degrees 2θ of, peaks in the x-ray powder diffraction pattern of FIG. 9. The isolated d-amphetamine carbamate in crystalline form may have an XRDP that is substantially the same as that of FIG. 9, with the peaks at approximately 9.2° and 11.5° 2θ being optional. The isolated d-amphetamine carbamate in crystalline form may have onsets substantially similar to those in the TG-DSC of FIG. 10. The calculated x-ray powder diffraction pattern generated from single-crystal data (FIG. 8) and the x-ray powder diffraction pattern of the synthesized d-amphetamine carbamate as shown in FIG. 9 contain different peaks, which suggests there may be different polymorphs of the amphetamine carbamate salt. The present disclosure includes all polymorphic crystalline forms.

In specific embodiments, the isolated amphetamine carbamate comprises or consists of l-amphetamine carbamate. In specific embodiments, the isolated amphetamine carbamate comprises l-amphetamine carbamate substantially free of amphetamine. In specific embodiments, the isolated amphetamine carbamate comprises l-amphetamine carbamate substantially free of d-amphetamine carbamate. In specific embodiments, the isolated amphetamine carbamate comprises l-amphetamine carbamate substantially free of amphetamine and substantially free of d-amphetamine carbamate.

The present disclosure includes d-amphetamine carbamate obtained by a process comprising removing a crystal comprised of d-amphetamine carbamate from a drug-containing polymer matrix comprising d-amphetamine in a polymer matrix. In specific embodiments, the polymer matrix comprises one or more acrylic pressure-sensitive adhesives. In some embodiments, the polymer matrix consists of the d-amphetamine, one or more acrylic pressure-sensitive adhesive, and d-amphetamine carbamate. In specific embodiments, the process comprises physically removing a crystal comprised of d-amphetamine carbamate from a drug-containing polymer matrix comprising d-amphetamine in a polymer matrix, such as by using tweezers to remove a crystal from the polymer matrix. Similar processes can be used to obtain l-amphetamine carbamate or mixtures of d-amphetamine carbamate and l-amphetamine carbamate, from a drug-containing polymer matrix comprising l-amphetamine or comprising l-amphetamine and d-amphetamine, respectively.

In other specific embodiments, the process comprises exposing d-amphetamine to carbon dioxide, which readily results in the formation of d-amphetamine carbamate. Similar processes can be used to obtain l-amphetamine carbamate or mixtures of d-amphetamine carbamate and l-amphetamine carbamate, by exposing l-amphetamine or a mixture of l-amphetamine and d-amphetamine, respectively, to carbon dioxide.

Methods of Detecting Amphetacarbamate

As noted above, the existence or identity of amphetamine carbamate and amphetacarbamate per se were not known. Rather, amphetamine carbamate was identified and characterized by analyzing crystals isolated from drug-containing polymer matrices of transdermal amphetamine compositions, and amphetacarbamate was identified via the work done to identify and characterize amphetamine carbamate. In order to develop transdermal amphetamine compositions and amphetamine transdermal delivery systems that have at most low levels of the newly discovered amphetamine-related compounds, amphetamine carbamate and amphetacarbamate, methods for detecting and quantifying amphetamine carbamate had to be developed. (Transdermal amphetamine compositions and amphetamine transdermal delivery systems that have at most low levels of amphetamine carbamate and amphetacarbamate are described in more detail in co-pending U.S. provisional application 63/134,847, filed Jan. 7, 2021 by Applicant Noven Pharmaceuticals, Inc., entitled "TRANSDERMAL AMPHETAMINE COMPOSITIONS WITH LOW LEVELS OF CARBAMATE," the entire contents of which are incorporated herein by reference, and in the PCT application claiming priority thereto.) The development of methods for detecting and quantifying amphetamine carbamate proved to be a particularly difficult undertaking for a number of reasons. For example, in solution, the amphetacarbamate moiety of the amphetamine carbamate salt is labile and readily converts to amphetamine. Thus, for example, typical HPLC assays could not be used.

Figure 2A:
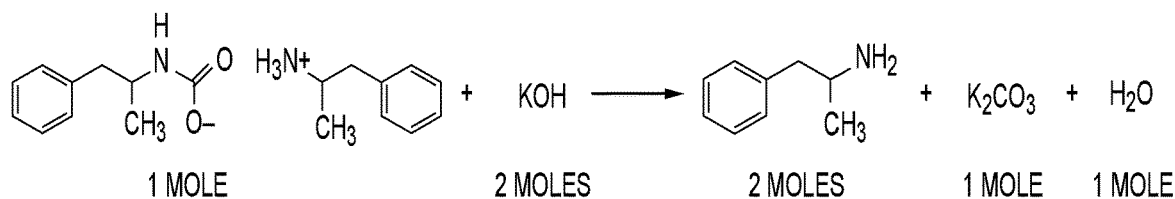
FIGS. 2A-2B illustrate reaction schemes for the reaction of amphetamine carbamate with potassium hydroxide (KOH) to yield amphetamine, potassium carbonate, and water.
Figure 2B:
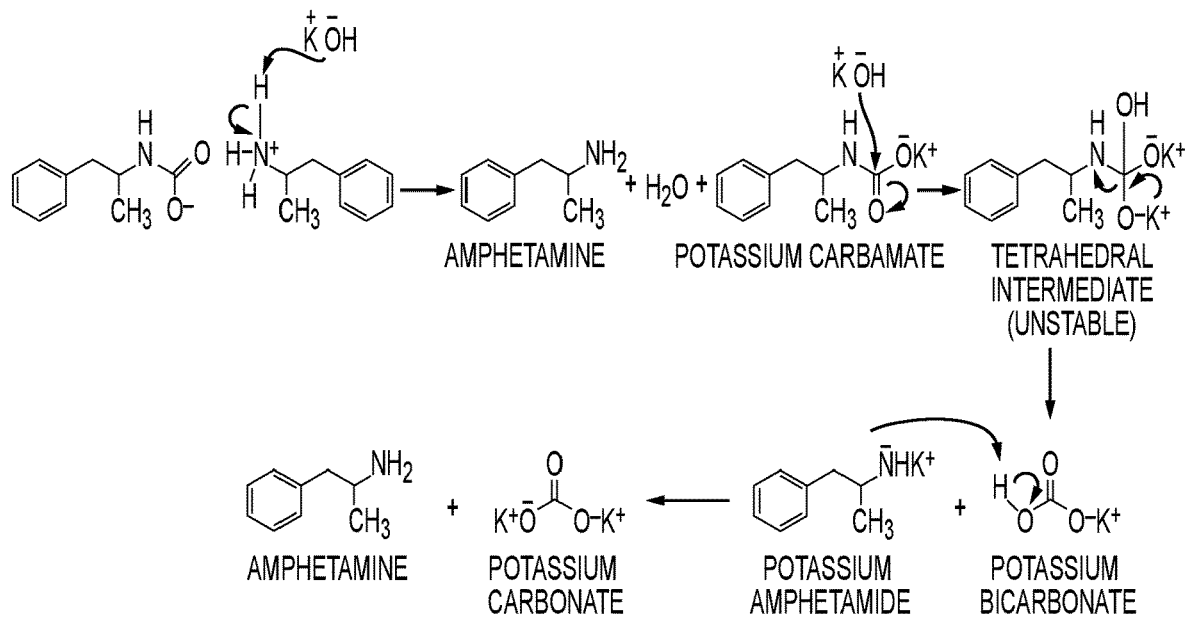

Faced with this problem, the present inventors developed and validated ion chromatography (IC) assays for amphetacarbamate. The assays are based on detection of carbonate ion generated from in situ reaction of amphetamine carbamate with a reagent that reacts in situ with the amphetacarbamate to produce carbonate ion, such as a base (e.g., potassium hydroxide or sodium hydroxide or lithium hydroxide). The reagent may be provided in situ by spiking the chromatography eluent with the reagent. While not wanting to be bound by theory, the current understanding of the reaction at issue is illustrated in FIG. 2A and FIG. 2B with reference to specific embodiments using KOH as the reagent. Again while not wanting to be bound by theory, and as depicted in FIG. 2B, it is believed that a first molecule of, e.g., KOH, acts as base and reacts with the acidic proton of the amphetammonium moiety of amphetamine carbamate to generate free amphetamine base and potassium carbamate. Then, a second molecule of, e.g., KOH, acts as a nucleophile and reacts with the electrophilic carbon atom of potassium carbamate to yield an unstable tetrahedral intermediate. The unstable tetrahedral intermediate readily decomposes into potassium bicarbonate and potassium amphetamide, which is a strong base. Then, potassium amphetamide acts as a base and reacts with the acidic hydrogen of potassium bicarbonate to generate a second molecule of amphetamine and potassium carbonate, which is the moiety detected and quantitated by IC. Therefore in the overall reaction, one mole of amphetamine carbamate reacts with two moles of, e.g., KOH, to yield two moles of amphetamine, one mole of potassium carbonate, and one mole of water, as set forth in FIG. 2A. The assay preferably is conducted under inert conditions, including conditions that minimize exposure of the test composition to the environment or other reactive species, to avoid or limit the production or introduction of additional amphetamine carbamate, amphetacarbamate and/or carbonate (other than the intended in situ production from reaction of amphetacarbamate).

Thus, certain embodiments of the present disclosure include methods of quantitatively determining the amount of amphetacarbamate in a composition, comprising (a) subjecting a composition comprising amphetacarbamate to reaction conditions that convert the amphetacarbamate in the composition into reaction products comprising carbonate; (b) quantifying the amount of carbonate in the reaction products; and (c) quantifying the amphetacarbamate originally present in the composition from the quantified amount of carbonate in the reaction products and the stoichiometric relationship between amphetacarbamate and carbonate in the reaction of step (a). In some embodiments, the reaction conditions comprise contacting the composition comprising amphetacarbamate with a reagent that reacts in situ with the amphetacarbamate to produce carbonate ion under an inert atmosphere. The reagent may be a base such as, for example, an aqueous alkali or earth alkali hydroxide salt, such as potassium hydroxide (KOH) or sodium hydroxide (NaOH) or lithium hydroxide (LiOH). In some embodiments, steps (a)-(c) are conducted in accordance with the IC assays described herein. Other specific and alternative aspects of suitable IC assays are discussed below.

Other embodiments of the present disclosure include methods of quantitatively determining the amount of amphetacarbamate in a composition by ion chromatography, comprising (a) subjecting a composition comprising amphetacarbamate to ion chromatography under an inert atmosphere with an eluent comprising a reagent that reacts in situ with the amphetacarbamate to produce carbonate ion; (b) separating the carbonate ion via a column packed with a composition comprising alkanol quaternary ammonium cation; (c) detecting and quantifying the carbonate ion with a conductivity detector; and (d) quantifying the amphetacarbamate originally present in the composition from the quantified amount of carbonate in the reaction products and the stoichiometric relationship between amphetacarbamate and carbonate in the reaction of step (a). Other specific and alternative aspects of suitable IC assays are discussed below.

Other embodiments of the present disclosure include methods of detecting the presence of amphetacarbamate in a composition comprising amphetamine by ion chromatography, comprising (a) subjecting a composition comprising amphetamine to ionic chromatography under an inert atmosphere with an eluent comprising an eluent comprising a reagent that reacts in situ with the amphetacarbamate to produce carbonate ion; (b) separating any carbonate ion via a column packed with a composition comprising alkanol quaternary ammonium cation; and (c) detecting any carbonate ion with a conductivity detector; wherein the detection of carbonate is indicative of the presence of amphetacarbamate in the composition. Other specific and alternative aspects of suitable IC assays are discussed below.

In any embodiments of the IC assays described herein, the IC eluent is inert-gas purged deionized water spiked with the reagent that reacts in situ with the amphetacarbamate to produce carbonate ion, such as a base, such as a base that provides a basic hydroxide ion, such as an aqueous alkali or earth alkali hydroxide salt, such as potassium hydroxide (KOH), sodium hydroxide (NaOH) or lithium hydroxide (LiOH). When the reagent is KOH, NaOH, or LiOH, the stoichiometric relationship between amphetacarbamate (or amphetamine carbonate) and carbonate ion for quantifying the amphetacarbamate (or, optionally, amphetamine carbonate) originally present in the composition from the quantified amount of carbonate ion in the reaction products is 1:1, as illustrated in FIG. 2A. The concentration of the reagent in the eluent may be any suitable concentration effective to react with any and all amphetacarbamate present in the test sample (composition at step (a)) to yield carbonate ion, under the conditions of the specific IC assay at issue (including, e.g., column size, flow rate, etc.). Example reagent concentrations include from about 1 mM to about 100 mM. including about 1, 5, 10, 15, 20, 25, 30, 35, 40, 45, 50, 75, or 100 mM, such as about 5, 10, 15, 20 or 25 mM. In certain embodiments, the eluent is inert-gas purged deionized water spiked with 10 mM KOH. The inert gas used for the inert-gas purged deionized water is not particularly limited, and may be, for example, helium.

As explained above, the IC assays disclosed herein are based on detection of carbonate ion (which has a molecular weight of 60.01 g/mol), generated from in situ reaction of amphetamine carbamate. Thus, any IC columns suitable for separating carbonate ion may be used, including an analytical column packed with a suitable resin and a guard column packed with a suitable resin. Suitable resins include those that are capable of separating inorganic anions in high-purity aqueous matrices, such as resins comprising alkanol quaternary ammonium cations as ion exchange groups. Specific examples of such resins include IonPac® AS17-C (analytical column) and IonPac® AG17-C (guard column). For example, for the stationary phase, a 250×4 mm analytical column (such as IonPac® AS17-C) and a 50×4 mm guard column (such as IonPac® AG17-C) may be used, both packed with alkanol quaternary ammonium resin having a particle size of 10.5 μm. The column(s) maybe maintained at any suitable temperature, such as a constant temperature of 30° C.±2° C. In use, an IC column may include the resin, an aqueous solution comprising the reagent, and two or more of amphetacarbamate, amphetamine, and carbonate ion, such as a column comprising (i) alkanol quaternary ammonium resin, (ii) KOH, NaOH or LiOH, and (iii) two or more of amphetacarbamate, amphetamine and carbonate ion. In some embodiments, the IC column comprises alkanol quaternary ammonium resin, KOH, amphetacarbamate, amphetamine, and carbonate ion. In some embodiments, the IC column comprises alkanol quaternary ammonium resin, KOH, amphetamine, and carbonate ion.

Any ion chromatographic system suitable for detecting and quantifying carbonate by the assays disclosed herein may be used. Thus, for example, the ion chromatographic system may include appropriate configurations suitable for the disclosed assays. Specific examples of suitable ion chromatographs include Dionex™ ICS-5000+ and ICS-6000 HPIC systems. In specific embodiments, the carbonate ion is detected and quantified using a conductivity detector. In further specific embodiments, such as may be implemented to increase sensitivity of carbonate ion detection, a suppressor is connected in series with and prior to the conductivity detector. For example, in some embodiments, the ion chromatograph is equipped with one or more of an autosampler (e.g., a Dionex™ AS-AP Autosampler), an eluent generator (e. g., Dionex™ EGC III KOH, Dionex™ EGC 400 KOH, Dionex™ EGC 500 KOH, Dionex™ EGC III NaOH, Dionex™ EGC III LiOH), a conductivity detector (e.g., Dionex™ ICS-6000 CD Conductivity Detector), and/or a suppressor (e.g., Dionex™ Anion Dynamically Regenerated Suppressor).

Other conditions/parameters of the IC assay and equipment can be selected, adjusted and controlled in accordance with standard practices in the art, keeping in mind a goal of avoiding or limiting conditions that might lead to the production or introduction of additional amphetamine, amphetamine carbamate, amphetacarbamate, and/or carbonate (other than the intended in situ production from reaction of amphetacarbamate), because such produced or introduced amphetamine, amphetamine carbamate, amphetacarbamate and/or carbonate would undermine the accuracy of the detection/quantitation results. For example, the conditions may be selected and controlled to prevent or limit exposure of any amphetamine present to carbon dioxide (because amphetamine may react with carbon dioxide to form additional amphetamine carbamate/amphetacarbamate), and/or may be selected and controlled to prevent or limit exposure to external sources of carbonate.

In some embodiments, the IC assay comprises assaying a series of standard carbonate solutions, each having a different predetermined concentration of carbonate ion, as working standard solution injections for preparation of a calibration curve. The predetermined concentrations of carbonate ion are selected to provide a calibration curve suitable for the test sample, i.e., having an appropriate range of carbonate ion concentrations around (above and below) the target, expected, or predicted carbonate concentration of the test sample. In such embodiments, a regression line of the carbonate ion peak area response (optionally corrected for any carbonate ion peak area response for a standard diluent blank as discussed below) versus carbonate concentration for the working standard solution injections can be plotted as a calibration curve. The amphetacarbamate concentration in the test sample can then be calculated based on the carbonate ion peak area response for the sample injection (optionally corrected for any carbonate ion peak area response for a sample blank as discussed below) with reference to the calibration curve.

Additionally or alternatively, a standard diluent blank and/or a sample blank can be assayed, to assess whether the solvent (diluent) used to prepare the working standard solutions and/or the solvent(s) and any other components used to prepare the sample, or any other aspects of the IC, are contributing to the carbonate ion peak area response. Typically, a standard diluent blank is a preparation of the solvent used to prepare the working standard solutions. Typically, a sample blank is a preparation of the components used to prepare the test sample, other than the test composition itself.

In some embodiments, the IC system suitability and peak symmetry are analyzed to assure that the system and methodology are functioning appropriately. For example, two or more injections of a carbonate working standard solution at the same predetermined concentration can be injected and the relative standard deviation of the carbonate ion peak area response can be assessed. In some embodiments, a relative standard deviation of the carbonate ion peak area response of 5% or less indicates that the system and methodology are functioning appropriately. In some embodiments, the regression coefficient is analyzed to assess suitability of the IC system. In some embodiments, a regression coefficient of not less than 0.990 indicates the system and methodology are functioning appropriately. Additionally or alternatively, in some embodiments, a standard carbonate solution at a predetermined concentration is used as a recovery standard to determine the percent recovery of carbonate ion. The percent recovery may be calculated as shown in the examples. In some embodiments, a percent recovery that does not exceed 15%, or that does not exceed 10%, or that does not exceed 5%, indicates the system and methodology are functioning appropriately. In some embodiments, the tailing factor of carbonate ion peak in the working standard solution injections is determined. In some embodiments, a tailing factor that does not exceed 2.0 indicates the system and methodology are functioning appropriately.

Amphetamine-Containing Compositions and Sample Preparation

In some embodiments of any of the detection/quantitation methods described herein, the composition at step (a) comprises amphetamine and amphetacarbamate. In some embodiments, the composition at step (a) is obtained from amphetamine API. In some embodiments, the composition at step (a) is obtained from a transdermal amphetamine composition or amphetamine transdermal delivery system. For example, the composition at step (a) may be a solution comprising amphetacarbamate and amphetamine prepared from an amphetamine-containing polymer matrix by a process comprising (i) immersing a drug-containing polymer matrix comprising amphetamine, amphetacarbamate, and polymer components in an organic solvent, to obtain an extraction mixture; (ii) subjecting the extraction mixture to sonication; (iii) adding a sample diluent (e.g., consisting of a mixture of the organic solvent and reagent grade water) to the extraction mixture to induce precipitation of the polymer components while maintaining the amphetamine and amphetacarbamate in solution, to obtain a composition comprising a precipitate; and (iv) filtering the composition comprising a precipitate to remove the precipitate, thereby obtaining a composition comprising amphetamine and amphetacarbamate in solution. The resulting composition, or a sample or aliquot thereof, can be used as the composition at step (a) of the detection/quantitation methods described herein.

In some embodiments of these embodiments, one or more of the sample preparation steps (e.g. one or more of steps (i)-(iv)) may be conducted under inert conditions, such as conditions that minimize exposure of the composition to, e.g., carbon dioxide, such as under an inert atmosphere (e.g., under nitrogen or argon gas), to avoid or limit the production or introduction of additional amphetamine carbamate, amphetacarbamate and/or carbonate, such as by avoiding or limiting reaction of amphetamine with carbon dioxide, which may form additional amphetamine carbamate/amphetacarbamate. (Such precautions also may be taken during any one or more or all steps of the IC assay.) Additionally or alternatively, the solvents used in one or more of the sample preparation steps may be solvent that has been purged with an inert gas. For example, the organic solvent maybe an inert gas-purged organic solvent, such as inert gas-purged methanol, such as helium-purged methanol. Additionally or alternatively, the sample diluent may be an inert gas-purged organic solvent, such as inert gas-purged methanol, such as helium-purged methanol, and reagent grade water. In specific embodiments, the sample diluent consists of a mixture of the same organic solvent used for step (i) and reagent grade water. Thus, for example, the organic solvent may be an inert gas-purged organic solvent, such as inert gas-purged methanol, such as helium-purged methanol, and the sample diluent consists of a mixture of the same organic solvent and reagent grade water.

Thus, to analyze a transdermal amphetamine composition or amphetamine transdermal delivery system for amphetamine carbamate/amphetacarbamate content, one or more of the following steps may be conducted in an inert atmosphere, such as under nitrogen or argon gas, to prepare a sample for IC analysis (e.g., for use as the composition at step (a)):

Remove any release liner present.

Optionally, apply the drug-containing polymer matrix (including the backing layer, if present) to a piece of filter paper previously sized to be slightly larger than the surface area of the drug-containing polymer matrix, and optionally hold the unit in place with, e.g., an appropriate number of paper clips.

Immerse the drug-containing polymer matrix (including the backing layer, if present) in an organic solvent in a closed glass jar, to obtain an extraction mixture.

Subject the extraction mixture to, e.g., sonication, to thoroughly expose/subject the polymer matrix components to the organic solvent.

Add a sample diluent to the extraction mixture to induce precipitation of the polymer components while maintaining the amphetamine and amphetacarbamate in the organic solvent, to obtain a composition comprising a precipitate.

Filter the composition comprising a precipitate (or an aliquot thereof) to remove the precipitate, thereby obtaining a composition comprising amphetamine and amphetacarbamate in the organic solvent.

For preparation of a sample blank for such a sample, the same steps would be followed without using the drug-containing polymer matrix. For example, if used, the same sized filter paper would be immersed in the same organic solvent, subject to the same sonication, addition of the same sample diluent, etc.

As noted above, the amount of amphetacarbamate originally present in the test sample (e.g., the composition at step (a)) is quantified from the quantified amount of carbonate ion in the reaction products using their molecular weights and the stoichiometric relationship between amphetacarbamate and carbonate in the reaction of step (a), which may depend on the reagent used, but typically will be 1:1 based on the reaction scheme set forth in FIG. 2A (which uses KOH as an example reagent). Examples of specific calculations are provided in the examples below.

Where applicable (e.g., where the test sample is prepared from a composition comprising amphetamine carbamate, such as an amphetamine drug-containing polymer matrix comprising amphetamine carbamate or a transdermal amphetamine composition or amphetamine transdermal delivery system comprising such a polymer matrix), parallel calculations may be used to determine the amount of amphetamine carbamate present in the original composition (e.g., amphetamine drug-containing polymer matrix or a transdermal amphetamine composition or amphetamine transdermal delivery system comprising such a polymer matrix) using the molecular weight of amphetamine carbamate instead of the molecular weight of amphetacarbamate in the calculations set forth below.

The following specific examples are included as illustrative of specific aspects of the IC assays described herein. These examples are in no way intended to limit the scope of the invention. Other aspects of the invention will be apparent to those skilled in the art to which the invention pertains.

EXAMPLES

Example 1—Detection of Amphetacarbamate in a Polymer Matrix by Ion Chromatography An example of a specific IC assay for quantitation of amphetacarbamate in a sample prepared from an amphetamine drug-containing polymer matrix is provided. Typical chromatograms for a standard diluent blank, a standard working solution, and a sample for such an assay is set forth in FIG. 11.

Sample and Sample Blank Preparation

Sample preparation is conducted under an inert gas, such as nitrogen or argon gas. A drug-containing polymer matrix is subject to dissolution/extraction in a closed glass jar using helium-purged methanol as an extraction solvent and subject to sonication. Then, helium-purged methanol/water (5%/95%) is added as a sample diluent to precipitate the adhesive components. In the calculations below, the total volume of the extraction solvent and sample diluent used (combined) is referred to as the Sample Volume. The sample (or an aliquot thereof) is filtered using a polytetrafluoroethylene (PTFE) filter and transferred to an IC tube for use in the IC assay. A sample blank is prepared by the same process, without using a drug-containing polymer matrix.

Standard and Standard Diluent Blank Preparation

Carbonate stock standard solutions and carbonate working standard solutions are prepared for purposes of creating a calibration curve.

To produce a Carbonate Stock Standard Solution, 27 mg of sodium carbonate is transferred into a 250 mL volumetric flask. 100 mL of Standard Diluent (helium-purged Methanol/Water, 30%:70%, v/v) is added to the flask and sonicated for five minutes to dissolve. The solution is allowed to cool inside a glove box under nitrogen and diluted to volume (250 mL) with Standard Diluent.

The carbonate ion concentration in the Carbonate Stock Standard Solution is calculated as follows:

$$\text{Carbonate Ion } (\mu g/mL) = \frac{(W)(\text{Potency})(0.56619)(1000)}{(250)}$$

W=weight of Sodium Carbonate Standard (mg) (27 mg in this example);
Potency=potency (purity) of sodium carbonate used;
0.56619=ratio of the molecular weights of carbonate ion to sodium carbonate;
1000=unit conversion of mg to µg; and
250=volume in mL.

Carbonate working standard solutions are prepared at appropriate concentrations to prepare a calibration curve for the test sample. For this example, working standard solutions are prepared as follows:

Working Standard A ("STD A") (Approximately 0.6 m/ml of Carbonate Ion): Pipette 2.0 ml of Stock Standard Solution into a 200 ml volumetric flask. Dilute to volume with Standard Diluent and mix well.

Working Standard B ("STD B") (Approximately 1.5 m/ml of Carbonate Ion): Pipette 5.0 ml of Stock Standard Solution into a 200 ml volumetric flask. Dilute to volume with Standard Diluent and mix well.

Working Standard C ("STD C") (Approximately 3 µg/ml of Carbonate Ion): Pipette 5.0 ml of Stock Standard Solution into a 100 ml volumetric flask. Dilute to volume with Standard Diluent and mix well.

Working Standard D ("STD D") (Approximately 5 µg/ml of Carbonate Ion): Pipette 4.0 ml of Stock Standard Solution into a 50 ml volumetric flask. Dilute to volume with Standard Diluent and mix well.

Standard D Recovery ("STD D Recovery") (Approximately 5 µg/ml of Carbonate Ion): Pipette 4.0 ml of Stock Standard Solution into a 50 ml volumetric flask. Dilute to volume with Standard Diluent and mix well.

A standard diluent blank is prepared by purging Methanol/Water (30%: 70%, v/v) with helium.

Ion Chromatography

The IC can be carried out using standard equipment, but adjustments are required to separate and quantify carbonate ions, as illustrated below.

Assay

The IC is set up with the following conditions.

For the stationary phase, a 250×4 mm analytical column (such as IonPac® AS17-C) and a 50×4 mm guard column (such as IonPac® AG17-C) is used, both packed with resin comprising alkanol quaternary ammonium cations as ion exchange groups with particle size of 10.5 µm. The columns are maintained at a constant temperature of 30° C.±2° C.

The eluent is helium-purged deionized water. For the in situ reaction, 10 mM potassium hydroxide is delivered into the eluent by an eluent generator. The reagent-spiked eluent (helium-purged deionized water spiked with 10 mM KOH) is pumped through the system at a constant flow rate of 1.0 mL/minute.

A conductivity detector is used for detection of carbonate ion in the eluent, with a sampling rate of 5 Hz. The detector cell heater temperature is set to 35° C. Sensitivity of carbonate ion detection is improved with the aid of a suppressor connected in series but prior to the detector (such as a Dionex ADRS 600 suppressor).

An injection volume of 100 μL is used with a run time of 25 minutes. The typical retention time for carbonate ion is 9-13 minutes. A typical relative retention time for nitrate ion that may be present is about 0.59 times that of carbonate ion, while a typical relative retention time for sulfate ion that may be present is about 1.72 times that of carbonate ion.

An exemplary chromatographic sequence is shown in Table 2, starting with the injections used to prepare the calibration curve. It should be understood that multiple blanks, standards, and/or sample injections can be used, with the average of the results of each type used in the calculations below. However, if only one blank injection of a given type yields a peak area for carbonate ion, use that peak area rather than an average.

TABLE 2

Exemplary Chromatographic Sequence(s) - Amphetamine Transdermal System

| Injection Number | Description |
| --- | --- |
| Standard Calibration Curve: | |
| 1 | Standard Diluent Blank |
| 2 | STD A |
| 3 | STD B |
| 4 | STD C |
| 5 | STD D |
| 6 | STD D Recovery |
| Sample Sequence: | |
| 1 | Sample Blank |
| 2 | Sample |
| 3 | Standard Diluent Blank |
| 4 | STD D Recovery |

Calculation of Amphetacarbamate

To determine the amount of amphetacarbamate in the sample, a power regression line is plotted of the carbonate ion peak area response versus concentration for the four working standard solutions injections (STD A, B, C and D). The y-intercept, slope and correlation coefficient of the regression line is calculated according to the following power equation:

$$y = ax^b \quad \text{(Equation 1)}$$

The above equation can be linearized by taking natural logarithm of both sides of the equation to yield equivalent equation (2) below:

$$\ln(y) = \ln(a) + b \ln(x) \quad \text{(Equation 2)}$$

where:
y=peak area response of carbonate ion from the working standard solution injection (e.g. STD A) minus peak area response of carbonate ion from the standard diluent blank injection. If no carbonate ion peak is detected in the standard diluent blank injection, use the peak area response from the working standard solution injection in the calculation;
x=concentration of carbonate ion in the working standard solution (μg/mL);
b=slope from regression line of standards; and
ln(a)=y-intercept.
Equation 2 can be rewritten as:

$$\ln(x) = \frac{\ln(y) - \ln(a)}{b}. \quad \text{(Equation 3)}$$

The concentration of carbonate (x), is expressed in exponential form of Equation 3 as shown below:

$$X = e^{\frac{\ln(y) - \ln(a)}{b}}.$$

The amount of amphetacarbamate present in the sample is calculated based on the amount of carbonate ion detected according to the top equation below (Equation 4A):

Equations 4A and 4B $$\text{mg Amphetacarbamate} = e^{\frac{\ln(A_{SPL}) - \ln(a)}{b}} \times \frac{V_{SAMP}}{1000} \times 2.96967$$

$$\% \text{ Amphetacarbamate} = \frac{\text{mg Amphetacarbamate}}{LC} \times 100$$

where:
$A_{SPL}$=peak area response of carbonate ion from the sample injection minus the peak area response of carbonate ion from the sample blank injection. If no carbonate ion peak is detected in the sample blank injection, then the peak area response from the sample solution injection is used in the calculation;
ln(a)=y-intercept;
b=slope;
$V_{SAMP}$=Sample Volume (mL) (see Sample Preparation step above);
1000=unit conversion from μg to mg; and
2.96967=ratio of the molecular weights of amphetacarbamate to carbonate ion (178.21/60.01).

The amount of amphetacarbamate present in the sample relative to the target amount of amphetamine present in the drug-containing polymer matrix used to prepare the sample (e.g., the "Label Claim" amount, or "LC") is calculated based on the amount of carbonate ion detected according to the top and bottom equations above (Equations 4A and 4B), where LC is the Label Claim amount of amphetamine (mg) in the drug-containing polymer matrix used, which is the target amount of amphetamine (mg) in the drug-containing polymer matrix used to prepare the sample (e.g., the patch or portion thereof used) (e.g., the amount that would be indicated as present on final product labeling, such as the FDA-approved product label), and 100 is the unit conversion to percent. Similar equations could be used to calculate the amount of amphetacarbamate present in the sample relative to a different basis, such as relative to the actual amount of amphetamine present in a drug-containing polymer matrix obtained from the same lot, or same region of the polymer matrix (as determined by HPLC, for example), or relative to the target amphetamine content of the dry polymer matrix (% wt/wt). Parallel calculations may be used to determine the amount of amphetamine carbamate present in the original composition by using the molecular weight of amphetamine carbamate instead of the molecular weight of amphetacarbamate in Equation 4B.

System Suitability

System suitability and peak symmetry can be evaluated to assure that the measuring system and the methodology are functioning appropriately. For example, successive injections of the same working standard solution (having the same predetermined carbonate ion concentration) can be made, and the relative standard deviation (RSD) of the peak area response of carbonate ion can be calculated and corrected for blank (standard diluent blank) as described above. Typically, it is desired that the % RSD does not exceed 5%. Typically, it is desired that the regression coefficient (r) is not less than 0.990. Additionally or alternatively, the % recovery of a carbonate working standard can be calculated as a check on the working standard, as illustrated by the Standard D Recovery solution in Table 2. In this example, the goal for the target % recovery for the Standard D Recovery solution injected following the four working standard solutions injections (STD A, B, C and D), is not to exceed 10%, while the goal for the target % recovery for the Standard D Recovery solution injected following the sample injection is to not exceed 15%.

$$\% \text{ Recovery} = \left| \frac{Conc._{STD} - Calc\ Conc._{STD}}{Conc._{STD}} \right| \times 100$$

where:
$Conc._{STD}$=Theoretical concentration of Standard D Recovery solution (µg/mL); and
Calc $Conc._{STD}$=Concentration of Standard D Recovery solution calculated from power regression curve.

$$Calc\ Conc_{STD} = e^{\frac{\ln(A_{STD}) - \ln(a)}{b}}$$

where:
$A_{STD}$=Peak area response of carbonate ion from the Standard D Recovery injection minus peak area response of carbonate ion from standard diluent blank injection. If no carbonate ion peak is detected in the standard diluent blank injection, the peak area response from the Standard D Recovery injection is used in the calculation;
ln(a)=y-intercept; and
b=slope.

The Tailing Factor (T) of the carbonate ion peak from standard solution injections can be assessed. A typical goal is that it does not exceed 2.0.

Example 2—Detection of Amphetacarbamate in Amphetamine API

Figure 12:
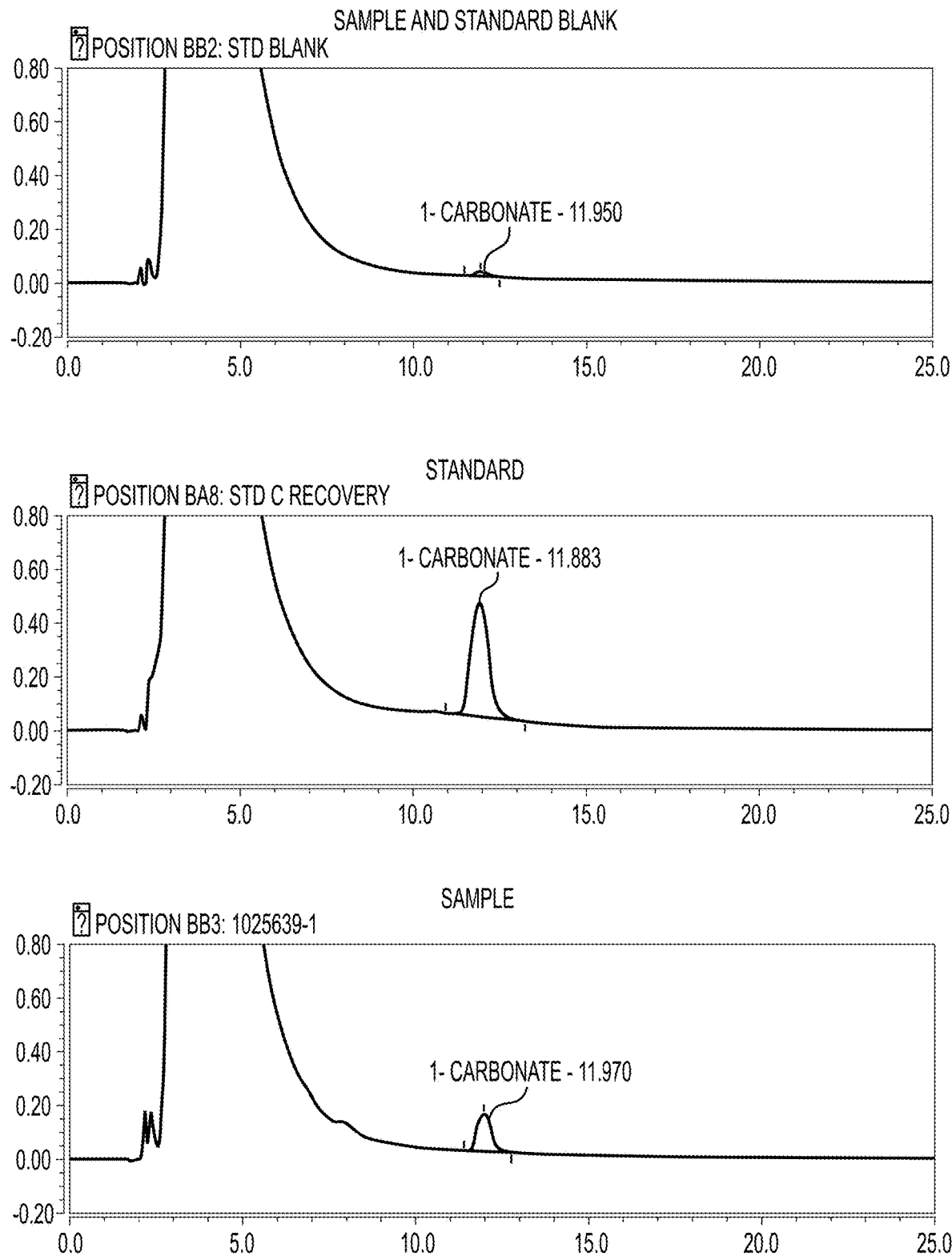
FIG. 12 sets forth a typical chromatogram for a sample/standard diluent blank ("Sample and Standard Blank"), a carbonate working standard solution ("Standard"), and a sample prepared from d-amphetamine active pharmaceutical ingredient ("API").

An IC assay as described herein can be used to detect or quantitate amphetacarbamate in amphetamine API. The IC assay is similar to that described for Example 1, except where noted below. A typical chromatogram for a sample and standard diluent blank ("Sample and Standard Blank"), a standard solution ("Standard") and a sample ("Sample") for such an assay is set forth in FIG. 12.

Sample Preparation

Sample preparation is conducted under an inert gas, such as nitrogen or argon gas. 300 mg of amphetamine API, such as d-amphetamine base or l-amphetamine base, is transferred into a 100 mL volumetric flask, diluted to volume (100 mL) with Sample Diluent (helium-purged Methanol/Water, 30%: 70%, v/v), and mixed well. In the calculations below, 100 mL is referred to as the Sample Volume. A portion of the sample solution is transferred into an IC vial for analysis.

Standard and Standard Blank Preparation

Carbonate stock standard solutions and carbonate working standard solutions are prepared for purposes of creating a calibration curve, as generally described in Example 1.

For the present example, Stock Standard Solutions (approximately 100 µg/ml carbonate ion) is produced as follows:

Accurately weigh approximately 35.4 mg of sodium carbonate and transfer into a 200 mL volumetric flask. Add approximately 100 mL of Standard Diluent to the flask and sonicate for five minutes to dissolve. Allow to cool inside a glove box under nitrogen. Dilute to volume (200 mL) with Standard Diluent.

For the present example, carbonate working standard solutions are prepared as follows:

Working Standard A (Approximately 1.5 µg/ml of Carbonate Ion): Pipette 3.0 ml of Stock Standard Solution into a 200 mL volumetric flask. Dilute to volume with Standard Diluent and mix well.

Working Standard B (Approximately 6 µg/ml of Carbonate Ion): Pipette 6.0 ml of Stock Standard Solution into a 100 mL volumetric flask. Dilute to volume with Standard Diluent and mix well.

Working Standard C (Approximately 12 µg/ml of Carbonate Ion): Pipette 12.0 ml of Stock Standard Solution into a 100 mL volumetric flask. Dilute to volume with Standard Diluent and mix well.

Working Standard D (Approximately 24 µg/ml of Carbonate Ion): Pipette 12.0 ml of Stock Standard Solution into a 50 mL volumetric flask. Dilute to volume with Standard Diluent and mix well.

Working Standard E (Approximately 30 µg/ml of Carbonate Ion): Pipette 15.0 ml of Stock Standard Solution into a 50 mL volumetric flask. Dilute to volume with Standard Diluent and mix well.

Standard C Recovery (Approximately 12 µg/ml of Carbonate Ion): Pipette 12.0 ml of Stock Standard Solution into a 100 mL volumetric flask. Dilute to volume with Standard Diluent and mix well.

A standard diluent blank is prepared by purging Methanol/Water (30%: 70%, v/v) with helium.

Ion Chromatography

The IC is set up as set forth in Example 1, except an injection volume of 25 µL is used. An exemplary chromatographic sequence is shown in Table 3, starting with the injections used to prepare the calibration curve. Because the sample preparation for this example only involves dilution with Sample Diluent, which is the same as the Standard Diluent, the standard diluent blank is used as the blank for both the calibration curve sequence and the sample sequence. As with Example 1, it should be understood that multiple blanks, standards, and/or sample injections can be used, with the average results of each type used in the calculations. However, as with Example 1, if only one blank injection of a given type yields a peak area for carbonate ion, use that peak area rather than an average.

TABLE 3

Exemplary Chromatographic Sequence(s) - Amphetamine API

| Injection Number | Description |
|---|---|
| Standard Calibration Curve: | |
| 1 | Standard Blank |
| 2 | STD A |
| 3 | STD B |
| 4 | STD C |
| 5 | STD D |
| 6 | STD E |
| 7 | STD C Recovery |
| Sample Sequence: | |
| 1 | Standard Blank |
| 2 | Sample |
| 3 | Standard Blank |
| 4 | STD C Recovery |

Calculation of Amphetacarbamate

To determine the amount of amphetacarbamate in the original sample, a power regression line is plotted from the peak area response of carbonate ion versus concentration for the five working standard solution (STD A, B, C, D and E) injections. The y-intercept, slope and correlation coefficient of the regression line are calculated according to the same power equations as in Example 1. The concentration of carbonate (x), is expressed in exponential form as in Equation 3 of Example 1. The % amphetacarbamate in the amphetamine API used to prepare the sample is calculated based on the amount of carbonate ion detected according to the equations below:

$$\text{mg Carbonate} = e^{\frac{\ln(A_{SPL}) - \ln(a)}{b}} \times \frac{V}{1000}$$

$$\% \text{ Amphetacarbamate} = \frac{\text{mg Carbonate} \times 2.96967}{W} \times 100$$

where:
$A_{SPL}$=Peak area response of carbonate ion from the sample injection minus peak area response of carbonate ion from the standard blank injection prior to the sample injection (if any);
$\ln(a)$=y-intercept;
b=slope;
V=Sample Volume (100 mL);
W=Sample Weight (mg) (300 mg in this example)
1000=unit conversion from µg to mg;
100=unit conversion to percent; and
2.96967=ratio of molecular weight of amphetacarbamate to molecular weight of carbonate ion (178.21/60.01).

System Suitability

System suitability and peak symmetry can be evaluated as discussed for Example 1. The % recovery of a carbonate working standard can be calculated as a check on the working standard, as illustrated by the Standard C Recovery solution in Table 3. In this example, the goal for the target % recovery for the Standard C Recovery solution is not to exceed 5%.

What is claimed is:

1. A method of quantitatively determining the amount of amphetacarbamate in a composition, comprising:
   (a) contacting a composition comprising amphetacarbamate with a source of basic hydroxide ions under an inert atmosphere to convert the amphetacarbamate in the composition into reaction products comprising carbonate;
   (b) quantifying the amount of carbonate in the reaction products; and
   (c) quantifying the amphetacarbamate originally present in the composition from the quantified amount of carbonate in the reaction products and the stoichiometric relationship between amphetacarbamate and carbonate in the reaction of step (a).

2. The method of claim 1, wherein:
   step (a) comprises subjecting the composition comprising amphetacarbamate to ion chromatography under an inert atmosphere with an eluent comprising a basic hydroxide ion under conditions that permit in situ reaction of the amphetacarbamate with the hydroxide ion to produce a carbonate ion;
   the method further comprises (a1) separating the carbonate ion via a column packed with a composition comprising an alkanol quaternary ammonium cation;
   step (c) comprises detecting and quantifying the carbonate ion with a conductivity detector; and
   step (d) comprises quantifying the amphetacarbamate originally present in the composition from the quantified amount of carbonate ion based on a 1:1 stoichiometric relationship between amphetacarbamate and carbonate.

3. A method of detecting the presence of amphetacarbamate in a composition comprising amphetacarbamate by ion chromatography, comprising:
   (a) subjecting a composition comprising amphetamine to ion chromatography under an inert atmosphere with an eluent comprising a basic hydroxide ion under conditions that permit in situ reaction of any amphetacarbamate present in the composition with the hydroxide ion to obtain a carbonate ion;
   (b) separating any carbonate ion via a column packed with a composition comprising an alkanol quaternary ammonium cation; and
   (c) detecting any carbonate ion with a conductivity detector;
   wherein detection of carbonate ion is indicative of the presence of amphetacarbamate in the composition.

4. The method of claim 3, wherein the composition at step (a) is a solution comprising amphetacarbamate and amphetamine prepared from an amphetamine-containing polymer matrix by a process comprising:
   (i) immersing a drug-containing polymer matrix comprising amphetamine, one or both of amphetammonium-amphetacarbamate and amphetacarbamate, and polymer components in an organic solvent, to obtain an extraction mixture;
   (ii) subjecting the extraction mixture to sonication;
   (iii) adding a sample diluent to the extraction mixture to induce precipitation of the polymer components while maintaining the amphetamine and amphetacarbamate in solution, to obtain a composition comprising a precipitate; and
   (iv) filtering the composition comprising a precipitate to remove the precipitate, thereby obtaining a composition comprising amphetamine and amphetacarbamate in solution.

5. The method of claim 4, wherein the amphetamine-containing polymer matrix comprises amphetamine carbamate having the following chemical structure:

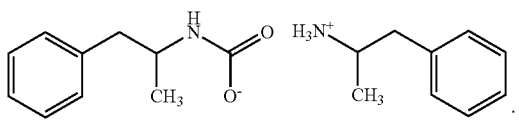

6. The method of claim 4, wherein one or more of steps (i)-(iv) are conducted under an inert atmosphere.

7. The method of claim 4, wherein the organic solvent is inert gas-purged methanol.

8. The method of claim 4, wherein the sample diluent consists of a mixture of the organic solvent and water.

9. The method of claim 4, wherein the organic solvent is inert gas-purged methanol and the sample diluent consists of a mixture of inert gas-purged methanol and reagent grade water.

10. The method of claim 4, wherein the organic solvent is helium-purged methanol and the sample diluent consists of a mixture of helium-purged methanol and reagent grade water.

11. The method of claim 4, wherein the amphetamine-containing polymer matrix is a drug-containing polymer matrix of an amphetamine transdermal delivery system.

12. The method of claim 4, wherein the composition at step (a) comprises l-amphetamine and the amphetacarbamate comprises l-amphetacarbamate.

13. The method of claim 3, wherein the composition at step (a) is a solution comprising amphetacarbamate and amphetamine prepared by dissolving an amphetamine active pharmaceutical ingredient composition (API) in an organic solvent.

14. The method of claim 13, wherein the organic solvent comprises inert gas-purged methanol.

15. The method of claim 13, wherein the API comprises l-amphetamine and the amphetacarbamate comprises l-amphetacarbamate.

16. The method of claim 13, wherein the API comprises d-amphetamine and the amphetacarbamate comprises d-amphetacarbamate.

17. The method of claim 13, wherein the API comprises d-amphetamine and the amphetacarbamate comprises d-amphetacarbamate.

18. The method of claim 13, wherein the API comprises amphetamine carbamate having the following chemical structure:

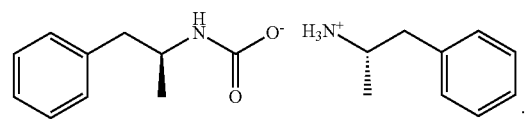

19. The method of claim 3, wherein the eluent is inert-gas purged deionized water spiked with KOH.

20. The method of claim 3, wherein the eluent is helium-gas purged deionized water spiked with KOH.

21. The method of claim 3, further comprising quantifying the carbonate ion with the conductivity detector.

22. The method of claim 21, further comprising quantifying the amphetacarbamate originally present in the composition from the quantified amount of carbonate ion based on a 1:1 stoichiometric relationship between amphetacarbamate and carbonate.

23. The method of claim 3, wherein the composition at step (a) comprises amphetamine and amphetacarbamate.

* * * * *

UNITED STATES PATENT AND TRADEMARK OFFICE
CERTIFICATE OF CORRECTION

PATENT NO. : 11,572,339 B2
APPLICATION NO. : 17/569872
DATED : February 7, 2023
INVENTOR(S) : Deboprosad Mondal Page 1 of 1

It is certified that error appears in the above-identified patent and that said Letters Patent is hereby corrected as shown below:

In the Claims

In Claim 2 at Column 22, Line 22, delete "step (c)" and insert --step (b)--.

In Claim 2 at Column 22, Line 24, delete "step (d)" and insert --step (c)--.

Signed and Sealed this
Twenty-fourth Day of September, 2024

Katherine Kelly Vidal
*Director of the United States Patent and Trademark Office*